(12) United States Patent
Kriesel et al.

(10) Patent No.: US 8,292,876 B2
(45) Date of Patent: Oct. 23, 2012

(54) SPECIAL PURPOSE FLUID DISPENSER WITH PRE-FILLED RESERVOIR

(76) Inventors: Marshall S. Kriesel, St. Paul, MN (US); Joshua W. Kriesel, San Francisco, CA (US); Thomas N. Thompson, Richfield, MN (US)

( * ) Notice: Subject to any disclaimer, the term of this patent is extended or adjusted under 35 U.S.C. 154(b) by 0 days.

(21) Appl. No.: 12/928,146

(22) Filed: Dec. 2, 2010

(65) Prior Publication Data

US 2011/0077593 A1    Mar. 31, 2011

Related U.S. Application Data

(62) Division of application No. 12/288,115, filed on Oct. 15, 2008.

(51) Int. Cl.
*A61K 9/22* (2006.01)

(52) U.S. Cl. ...... 604/891.1; 604/132; 604/9; 604/890.1; 604/134; 604/135; 604/136; 604/137; 604/138; 604/139; 604/140; 604/141; 604/142; 604/143; 604/151; 604/153; 604/156; 604/164.02; 604/164.09; 604/30; 604/236; 604/527; 604/323

(58) Field of Classification Search ........... 604/9, 890.1, 604/891.1, 134–143, 151, 153, 156, 164.02, 604/164.09, 30, 236, 537, 323; 222/207, 222/209, 213
See application file for complete search history.

(56) References Cited

U.S. PATENT DOCUMENTS

| | | | | |
|---|---|---|---|---|
| 3,568,889 | A * | 3/1971 | Morane | 222/136 |
| 3,794,068 | A * | 2/1974 | Milroy | 137/497 |
| 5,395,340 | A * | 3/1995 | Lee | 604/151 |
| 5,499,968 | A * | 3/1996 | Milijasevic et al. | 604/30 |
| 5,607,418 | A * | 3/1997 | Arzbaecher | 604/891.1 |
| 6,416,495 | B1 * | 7/2002 | Kriesel et al. | 604/132 |
| 2005/0277882 | A1 * | 12/2005 | Kriesel | 604/131 |
| 2007/0219501 | A1 * | 9/2007 | Kriesel et al. | 604/185 |

* cited by examiner

*Primary Examiner* — Theodore Stigell
*Assistant Examiner* — Scott Medway
(74) *Attorney, Agent, or Firm* — James E. Brunton

(57) ABSTRACT

A compact, nonelectric fluid dispenser for use in controllably dispensing beneficial agents such as propofol and dexmedetomidine hydrochloride to patients. The dispenser includes a fluid flow control assembly that precisely controls the flow of the medicament solution to the patient and embodies a collapsible, pre-filled drug container that contains the beneficial agents to be delivered to the patient. The unit-dose fluid dispenser of the invention is presented in a sterile and aseptic manner, where the drug has been pre-filled in the system, so that the practitioner cannot mistakenly give the wrong drug to the patient. The dispenser uniquely provides a more efficient medicament delivery system for procedure rooms, such as the endoscopy center, so that a greater number of patients can be treated per day at a higher standard of care with increased profits for the healthcare provider.

9 Claims, 38 Drawing Sheets

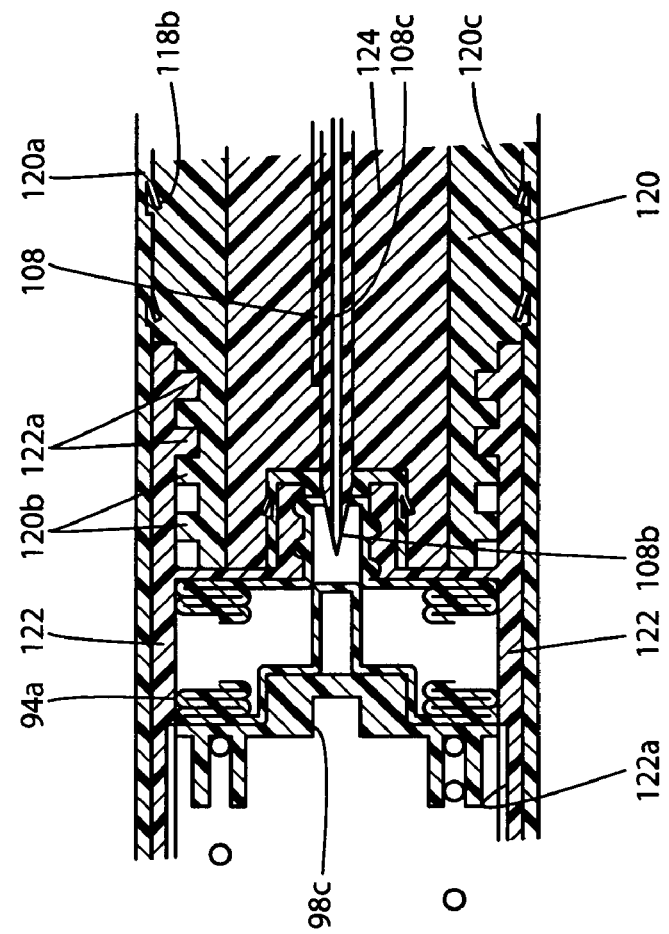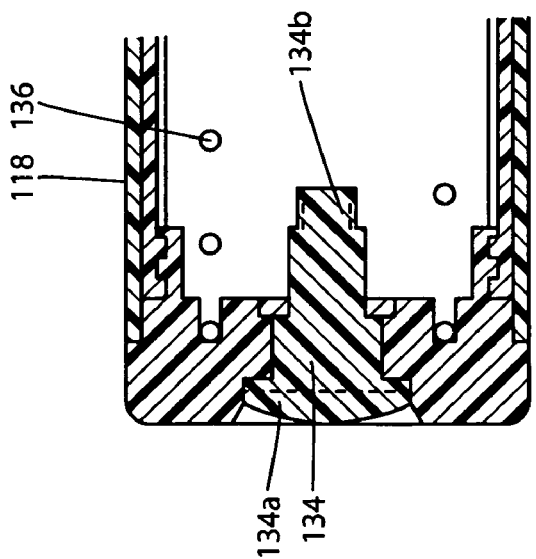
FIG. 20

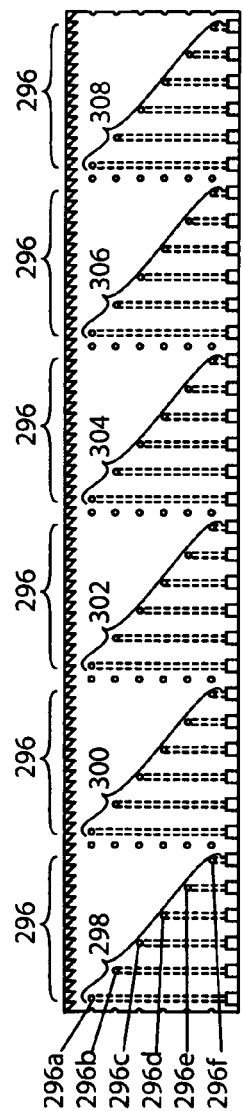
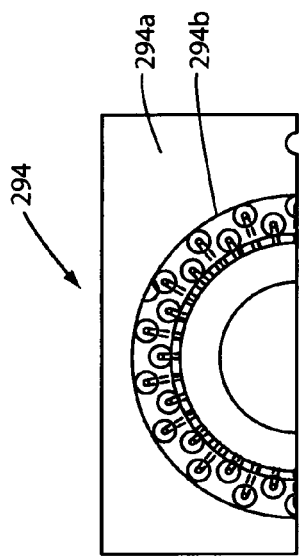
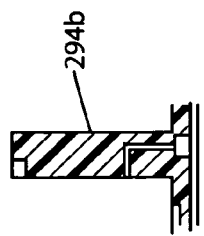
FIG. 30
FIG. 28
FIG. 29

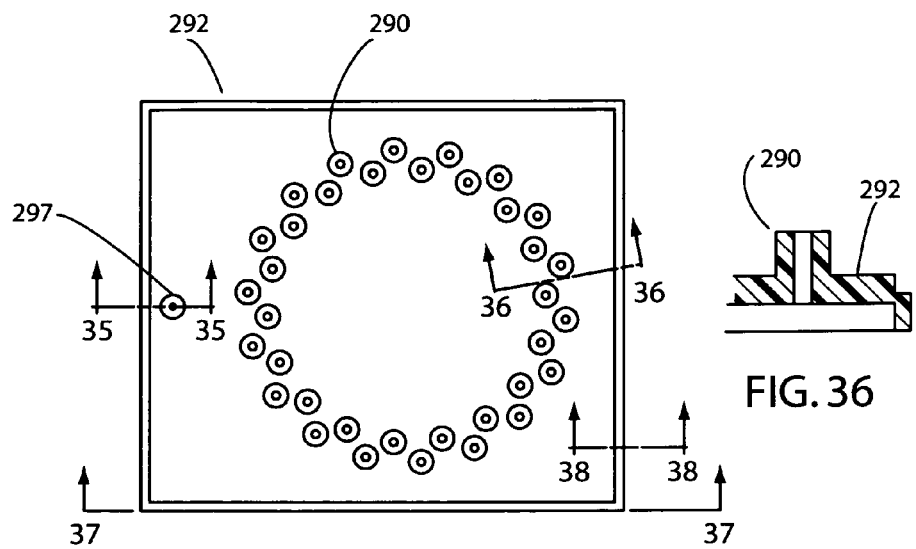
FIG. 34
FIG. 36
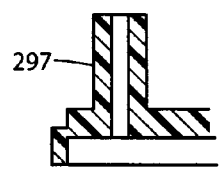
FIG. 35
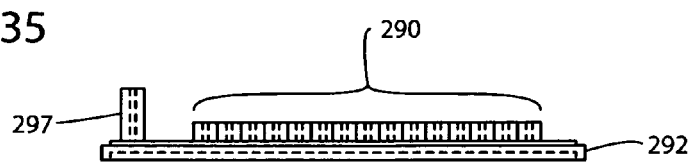
FIG. 37
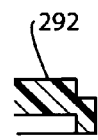
FIG. 38

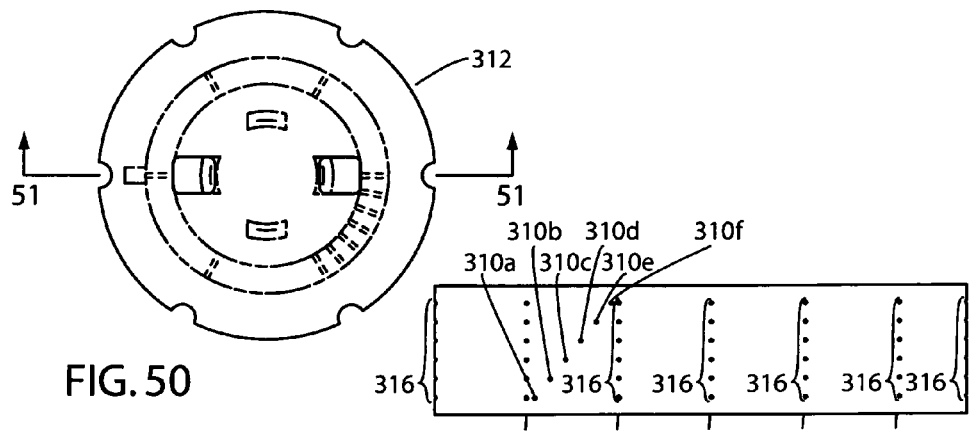
FIG. 50
FIG. 51A
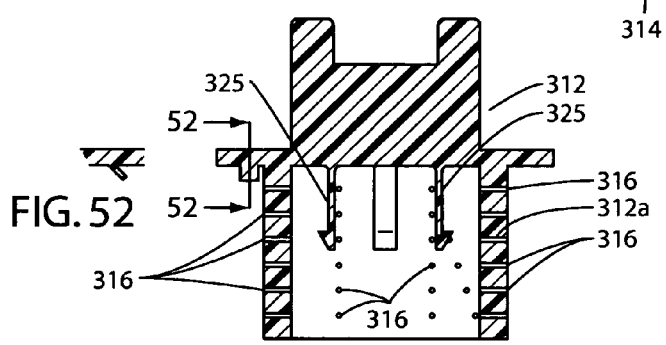
FIG. 52
FIG. 51
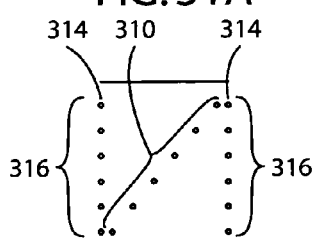
FIG. 53A
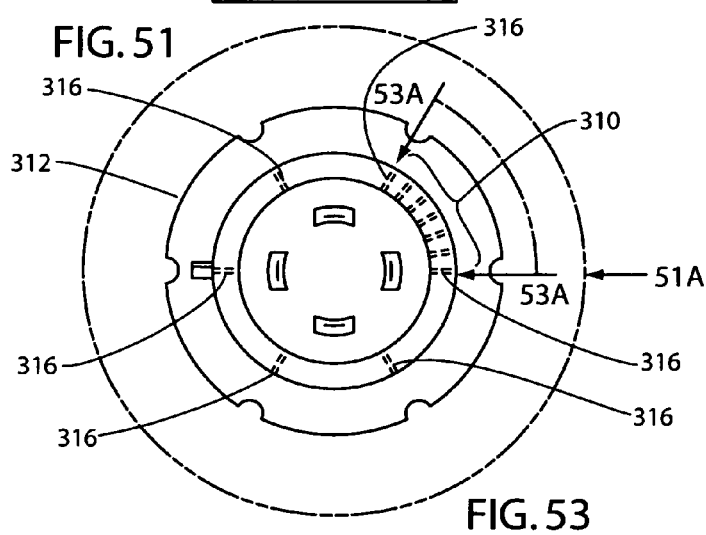
FIG. 53

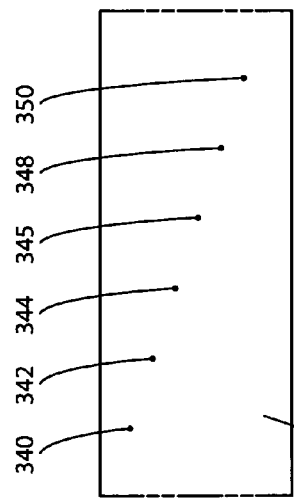
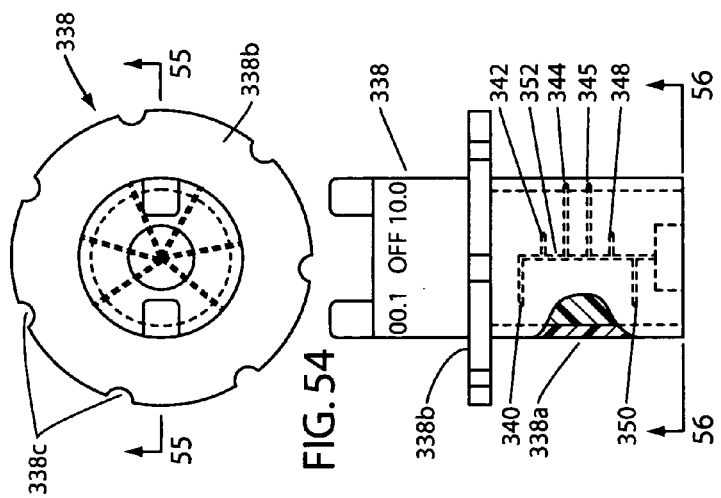
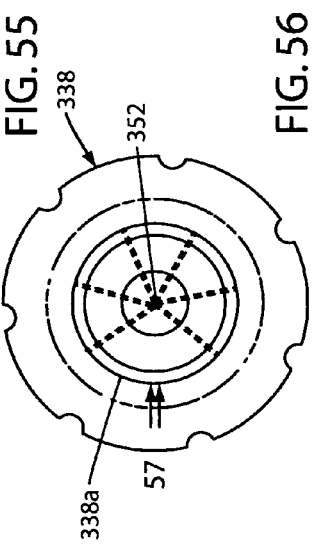

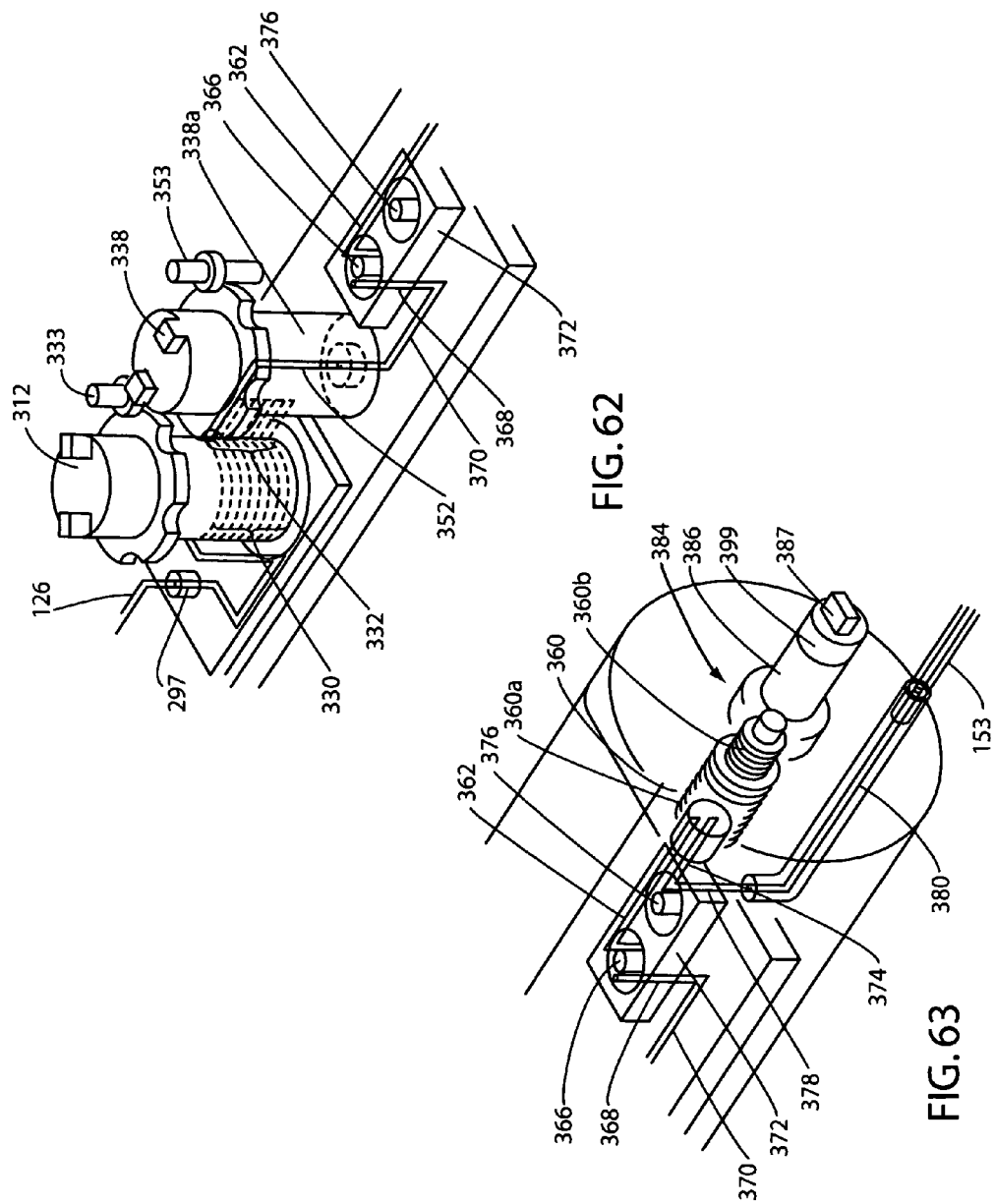

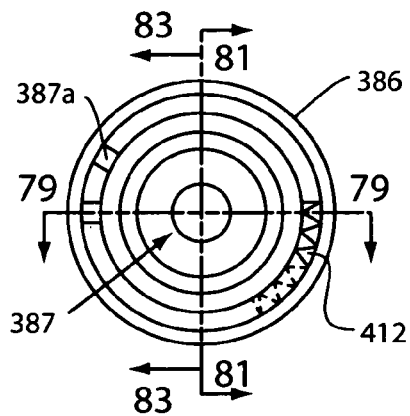
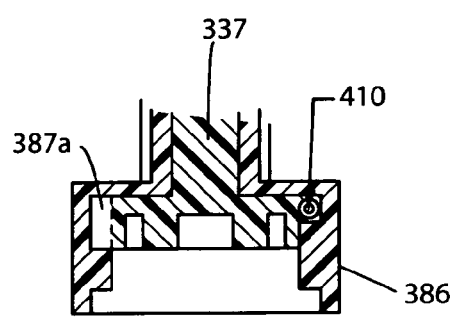
FIG. 78   FIG. 79
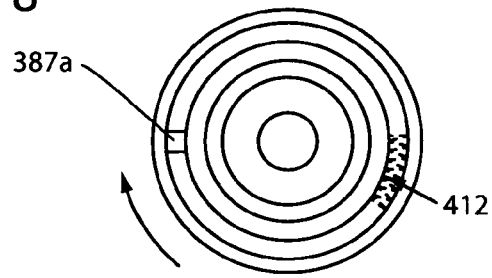
FIG. 80
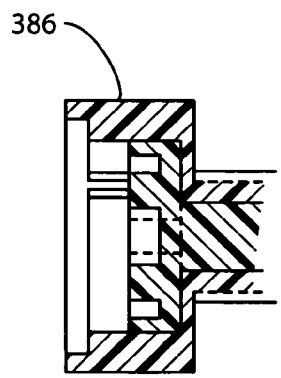 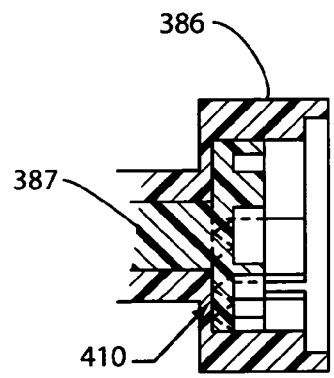
FIG. 81   FIG. 82

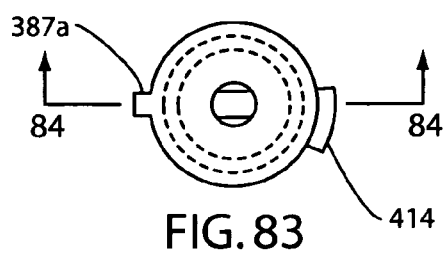
FIG. 83
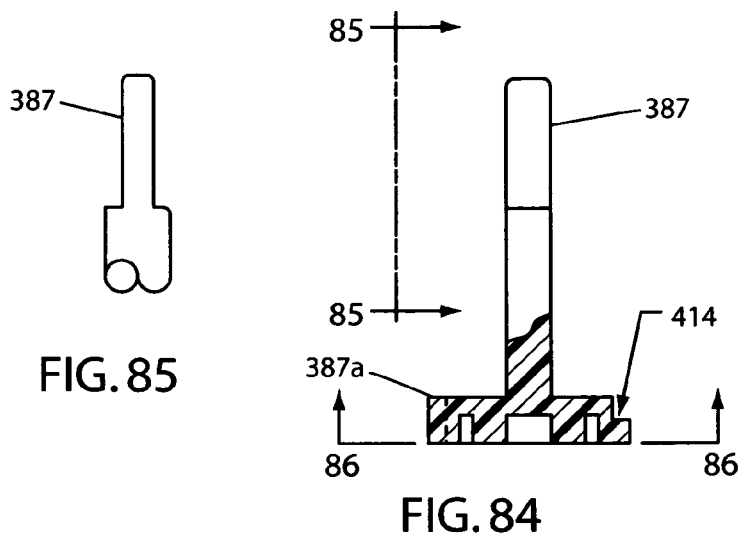
FIG. 85
FIG. 84
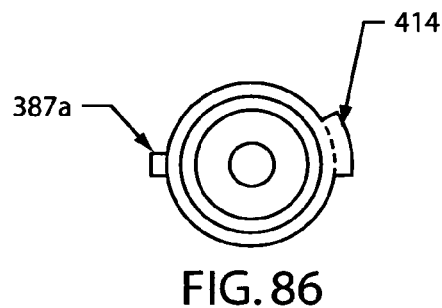
FIG. 86

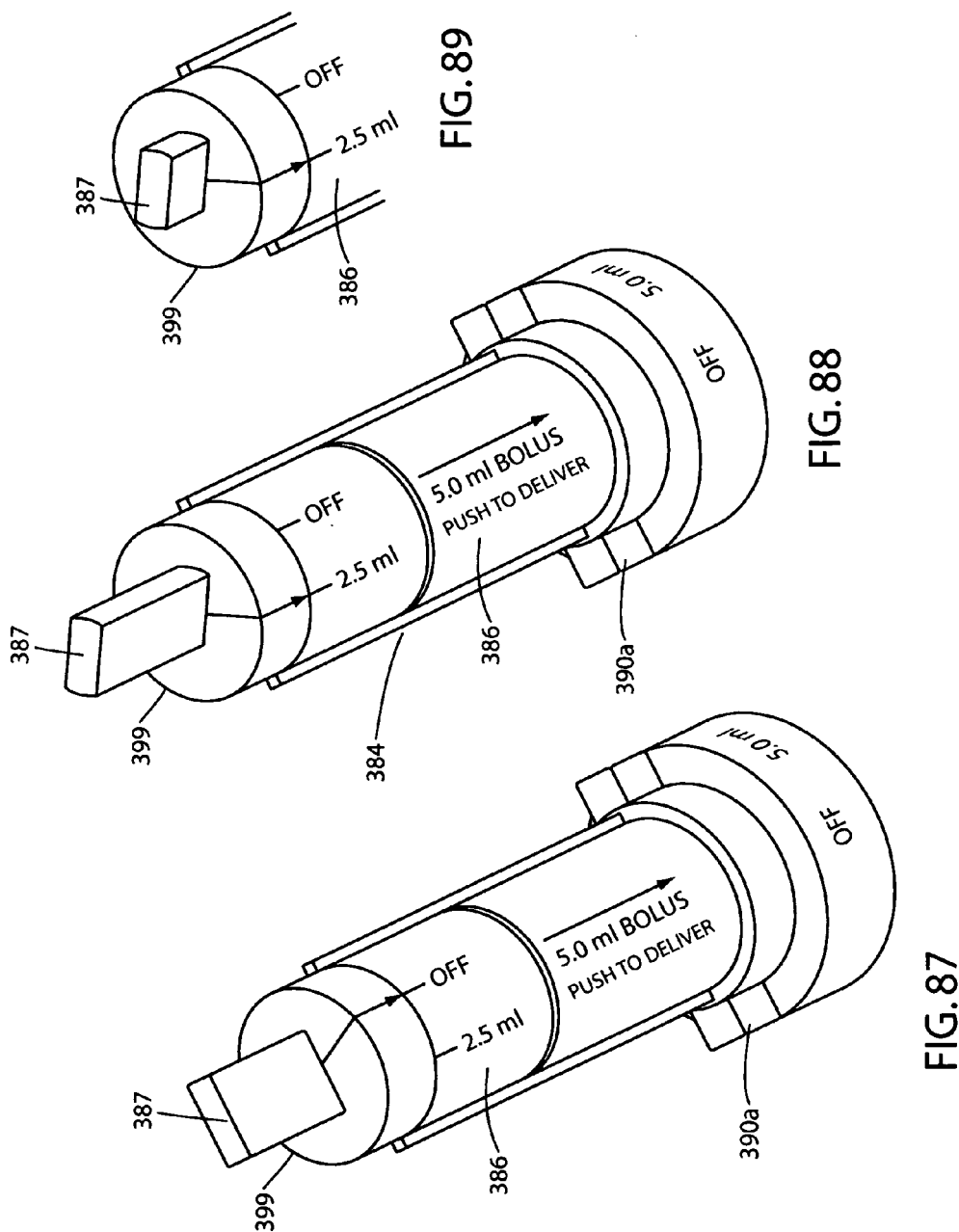

SPECIAL PURPOSE FLUID DISPENSER WITH PRE-FILLED RESERVOIR

CROSS-REFERENCE TO RELATED APPLICATIONS

This is a divisional application of co-pending application U.S. Ser. No. 12/288,115 filed Oct. 15, 2008.

STATEMENT REGARDING FEDERALLY SPONSORED RESEARCH OR DEVELOPMENT

Not Applicable

INCORPORATION-BY-REFERENCE OF MATERIAL SUBMITTED ON A COMPACT DISC

Not Applicable

BACKGROUND OF THE INVENTION

1. Field of the Invention

The present invention relates generally to fluid dispensing devices. More particularly, the invention concerns a novel dispenser for dispensing propofol, as well as analogous sedation agents, to patients with increased safety and efficiency, while reducing the probability of hospital acquired infections.

2. Description of Related Art Including Information Disclosed Under 37 CFR 1.97 and 1.98

A number of different types of medicament dispensers for dispensing various types of medicaments to patients have been suggested in the past. The traditional prior art infusion methods make use of a flexible infusion bag suspended above the patient. Such gravametric methods are cumbersome, imprecise, require many time consuming steps by clinicians, are susceptible to medication errors and require bed confinement of the patient. Periodic monitoring of the apparatus by the nurse or doctor is required to detect malfunctions of the infusion apparatus. Accordingly, the prior art devices are not well suited for use in those instances where the patient must be transported from one part of the healthcare facility to another.

Many of the state-of-the-art medicament delivery devices involve the use of electronic pumps to dispense the medicament from the dispenser reservoir. In the past, these types of devices have been the devices of choice for dispensing propofol (and other injectable sedation agents) and this equipment requires significant effort to prepare and administer the drug.

Propofol is a highly protein bound in vivo and is metabolized by conjugation in the liver. Its rate of clearance exceeds hepatic blood flow, suggesting an extrahepatic site of elimination as well. Its mechanism of action is uncertain, but it is postulated that its primary effect may be potentiation of the GABA—a receptor, possibly by slowing the closing channel time. Recent research has also suggested the endocannabinoid system may contribute significantly to propofol's anesthetic action and to its unique properties.

In recent years propofol has been widely used as an anesthetic agent for the induction of general anesthesia in adult patients and pediatric patients older than 3 years of age, for use in the maintenance of general anesthesia in adult patients and pediatric patients older than 2 months of age, for use in sedation for intubated, mechanically ventilated adults, and in procedures such as colonoscopy.

At the present time, propofol is commonly delivered through an electronic pump that is preset with the patient's weight (in kg) and a dosage increment measured in micrograms/kg/min. One prior art electronic pump that is presently in use is a pump sold by Baxter International, Inc, of Deerfield, Ill. under the name and style "InfusO.R.". This pump contains four separate dials. The first dial is to set the patient weight; the second dial is to set the dosage; the third dial is to set a bolus volume to initiate sedation; and the fourth dial is used to purge the syringe if there is any remaining propofol after the procedure. The Baxter pump has a magnetic plate that contains all the increments of the dials and the plates can be changed for different medications. By having removable plates, there is an increased possibility of medication error if the magnetic plate is not checked for increments for the correct medication or the correct concentration. The Baxter pump is typically used in the surgicenter setting where the anesthesiologist gives the patient an initial bolus of propofol for inducing sedation and the preset dosage is given in addition to gas anesthesia to keep the patient asleep during the operation.

Another pump that is presently in use is a pump sold by the Cardinal Health Company of Dublin, Ohio under the name and style "ALARIS PL". The ALARIS PL syringe pump or ALARIS IVAC pump is used in conjunction with a Diprifusor syringe that is pre-filled with propofol. The Diprifusor is a target controlled infusion (TCI) system that was developed to enhance the control of IV anesthesia. With a TCI pump, a microprocessor manages the infusion rate and controls the syringe. The anesthesiologist enters the body weight of the patient, the age of the patient, and the dosage in microgram/ml. The Alaris pumps rely on the anesthesiologist entering the correct data minimizing the possibility of medication error but the dosage form is not the commonly used increment, (microgram/ml instead of microgram/kg/min) which relies on the anesthesiologist to convert the dosage and potentially increases the risk of medication error through miscalculation. The Diprifusor and TCI pumps are typically used in Europe where the pump is used to control sedation and anesthesia, but are thus far not dominant in the American surgical market.

Many current disposable infusion pump modalities also require the disposable pump to be filled by an attending clinician. These filling and preparation protocols present a number of serious challenges that can lead to serious medication errors, patient injury, or patient death. For example, a medication error can result from the clinician accidentally putting the wrong medicine into the delivery system. Additionally, filling an infusion pump in a non-aseptic environment (e.g. the operating room) can also pose challenges in maintaining drug and device sterility.

As will be discussed in greater detail hereinafter, the propofol dispenser of the present invention allows the anesthesiologist to create a basic "recipe" for propofol based sedation that could prevent patient complications. The dispenser of the present invention is particularly well-suited for use in the administration of propofol by non-anesthesiologists in low risk procedures, such as colonoscopies.

Another pharmaceutical agent appropriate for use in this novel dispenser technology is dexmedetomidine hydrochloride (Precedex), and related compounds. Precedex is indicated for sedation of initially intubated and mechanically ventilated patients during treatment in an intensive care setting. Precedex is typically administered by continuous infusion using a syringe of the drug fluid (drawn up in a non-aseptic environment by the anesthesiologist) and dispensed by an electronic pump. Precedex is being used with patients in the intensive care unit (ICU), during neurosurgery and for children during MRI.

Precedex is delivered via intravenous infusion over a selected amount of time through a controlled infusion with the use of an electronic or battery operated pump or with a "smart pump". A pre-filled and non-electric pump that is therapy specific could allow more widespread use of novel sedation agents (such as Precedex), because of the ability to administer the therapy in a safer and more efficient manner without the need for multiple steps and sophisticated software routines.

The novel dispenser of the present invention provides numerous advantages over prior art devices including the following:

Creation of a standard operating procedure for the administration of propofol by anesthesiologists and non-anesthesiologists alike.

Elimination of the need for filling syringes, thereby reducing the potential for medication errors due to filling (i.e. using the wrong concentration of propofol) or use of a drug that is similar in appearance to propofol.

Elimination of the need for an electronic pump, thereby reducing the potential for medication error due to incorrect settings.

Reducing costs to healthcare providers and practitioners by eliminating expensive electronic capital equipment that requires continuous maintenance, calibration and cleaning.

Elimination of the requirement for electricity in austere or chaotic environments (e.g. during military engagements, natural disasters).

Presentation of the sedation agent at the point of care in an aseptic manner as a single self-contained unit-dose pre-filled delivery system should also minimize the probability of hospital acquired infection.

As previously mentioned, a significant market for the pre-filled unit-dose small volume dispenser of the present invention is the endoscopy center market. In this regard, one form of the dispenser of the present invention is specially designed for relatively short procedures (i.e. 20-30 minutes), such as colonoscopies and endoscopies. More particularly, the dispenser of the invention, which is non-electric and disposable following use, can provide an extremely cost effective means of increasing efficiency in the endoscopy center. The dispenser uniquely provides an alternative to expensive electronic pumps that are often complicated and time consuming to operate. In addition, low cost disposable devices for use in outpatient clinics are consistent with a broader theme in healthcare that is aimed at lowering costs while improving quality of care and patient outcomes. Because physicians in the endoscopy center are searching for a cost effective means to increase patient throughput within the center, the dispenser of the present invention provides a natural fit for a standardized sedation process for colonoscopies and endoscopies, without compromising the quality and safety of the procedure.

In another form of the present invention, the dispenser comprises a mid-volume propofol delivery systems technology (65 ml) that is specially designed for use in the surgicenter for procedures that require sedation times of 1-2 hours. In this application a novel dispenser can serve as a safe and effective means for patients that are to be fitted with orthopedic and cardiac implants. Similarly, this novel mid-volume dispenser can function well with minimum discomfort for general surgeries such as hernia repairs and the like. Because physicians in the surgicenter market are often quite time conscious, the dispenser of the present invention comprises a natural fit for a standardized sedation process that could potentially increase patient throughput within the market without compromising the quality and safety of the procedure. Additionally, patients prefer propofol as an anesthetic agent because there is no "hangover" effect, which stems from its ease of titration and rapid elimination half-life. By way of comparison, traditional anesthesia with gas has a very slow elimination half-life and patients require long recovery times that are typically complicated by nausea and vomiting. Conversely, propofol has inherent antiemetic properties, which chemically combats feelings of nausea.

In yet another form of the present invention, the dispenser comprises a large volume propofol dispenser (250 ml) that is specially designed for use in military applications, including total IV anesthesia (TIVA) by the Forward Surgical Team at the battlefield, as well as for sedation of the patient during transport from one echelon of care to the next. This form of the invention can provide a safe and effective means to sedate a patient during an operation and throughout transport without relying on bulky medical equipment or expensive equipment that is transported with the patient and never returned to the original care facility.

As will be fully appreciated from the discussion that follows, the devices of the present invention are also particularly useful in ambulatory situations. The ability to quickly and efficaciously treat wounded soldiers, especially in unpredictable or remote care settings, can significantly improve chances for patient survival and recovery. Accurate intravenous (IV) drug and fluid delivery technologies for controlling pain, preventing infection, and providing a means for IV access for rapid infusions during patient transport are needed to treat almost all serious injuries.

It is imperative that battlefield medics begin administering life saving medications as soon as possible after a casualty occurs. The continuous maintenance of these treatments is vital until higher echelon medical facilities can be reached. A compact, portable and ready to use infusion device that could be easily brought into the battlefield would allow medics to begin drug and resuscitation agent infusions immediately. Additionally, it would free them to attend to other seriously wounded patients who may require more hands-on care in the trauma environment following triage. In most serious trauma situations on the battlefield, IV drug delivery is required to treat fluid resuscitation, as well as both pain and infection. Drug infusion devices currently available can impede administration of IV infusions in remote care settings.

Expensive electronic infusion pumps are not a practical field solution because of their weight and cumbersome size. Moreover, today's procedures for starting IV infusions on the battlefield are often dangerous because the attending medic must complete several time consuming steps. The labor intensive nature of current gravity solution bag modalities can prevent medics from attending to other patients also suffering from life threatening injuries. In some cases, patients themselves have been forced to hold flexible infusion bags elevated, in order to receive the medication by gravity drip.

BRIEF SUMMARY OF THE INVENTION

By way of brief summary, one form of the dispensing device of the present invention for dispensing the beneficial agent, such as propofol, to a patient comprises a housing, a carriage assembly disposed within the housing, a pre-filled drug reservoir assembly carried by the carriage, a stored energy means operably associated with the carriage for moving the carriage between a first position and a second position to expel from the reservoir the fluid medicament contained therein, and flow control means to control the flow of fluid from the reservoir, the flow control means uniquely comprising dose control means for controlling the dose of medicament to be delivered to the patient and rate control means for controlling the rate of medicament flow to the patient. This novel design would therefore allow the physician to set a medicament flow rate based on the patient's body weight in kg and the patient appropriate dose in micrograms per kg per hour.

With the forgoing in mind, it is an object of the present invention to provide a compact, nonelectric fluid dispenser for use in controllably dispensing propofol to patients.

Another object of the invention is to provide a fluid dispenser of simple construction that can be used in the field with a minimum amount of training.

Another object of the invention is to allow infusion therapy to be initiated quickly and easily on the battlefield so that the attending medic or medical professional can more efficiently deal with triage situations in austere environments.

Another object of the invention is to provide a dispenser of the class described which includes a fluid flow control assembly that precisely controls the flow of the medicament solution to the patient.

Another object of the invention is to provide a dispenser that includes precise variable flow rate selection.

Another object of the invention is to provide a fluid dispenser of simple construction, which embodies a collapsible, pre-filled drug container that contains the beneficial agents to be delivered to the patient.

Another object of the invention is to provide a fluid dispenser of the class described which is compact, lightweight, is easy and safe for providers to use, is fully disposable, transportable, and is extremely reliable in operation.

Another object of the invention is to provide a unit-dose fluid dispenser of the class described that is presented in a sterile and aseptic manner, where the drug has been pre-filled in the system, so that the practitioner cannot mistakenly give the wrong drug to the patient.

Another object of the invention is to provide a medicament dispenser that improves the process efficiency of the healthcare setting by streamlining the tasks associated with the preparation, administration and monitoring of drug delivery of regimen.

Another object of the invention is to provide a low cost single-use alternative to expensive electronic pumps that have to be continually cleaned, calibrated and maintained at tremendous costs to healthcare providers.

Another object of the invention is to provide a dispenser that can administer anesthesia and sedation agents to patients without problematic side effects, such as nausea and vomiting, typically encountered with traditional gas anesthesia.

Another object of the invention is to provide a more efficient medicament delivery system for procedure rooms, such as the endoscopy center, so that a greater number of patients can be treated per day at higher standard of care with increased profits for the healthcare provider.

Another object of the invention is to provide a fluid dispenser as described in the preceding paragraphs that is easy and inexpensive to manufacture in large quantities.

BRIEF DESCRIPTION OF SEVERAL VIEWS OF THE DRAWINGS

FIG. 20 is a longitudinal cross-sectional view similar to FIG. 4, but showing the advancement of the piercing needle component of the fluid dispensing device into piercing engagement with the elastomeric seal provided in the neck of the fluid reservoir component and into piercing engagement with the closure wall of the fluid reservoir component.

FIG. 28 is a fragmentary view taken along lines 28-28 of FIG. 27 showing only one half of the main fluid pickup housing and illustrating the construction of the anti-rotational grooves thereof.

FIG. 29 is a cross-sectional view taken along lines 29-29 of FIG. 28.

FIG. 30 is a generally diagrammatic view illustrating the main fluid pickup housing of the device shown in the upper portion of FIG. 27 as it would appear in flat configuration.

FIG. 34 is a top plan view of the upper rate control plate of the patient weight selector subassembly illustrated in FIG. 25.

FIG. 35 is a cross-sectional view taken along lines 35-35 of FIG. 34.

FIG. 36 is a cross-sectional view taken along lines 36-36 of FIG. 34.

FIG. 37 is a view taken along lines 37-37 of FIG. 34.

FIG. 38 is a cross-sectional view taken along lines 38-38 of FIG. 34.

FIG. 50 is a top plan view of the patient weight selector knob of the patient weight selector subassembly of the fluid delivery device.

FIG. 51 is a cross-sectional view taken along lines 51-51 of FIG. 50.

FIG. 51A is a generally diagrammatic view illustrating the portion of the patient weight selector knob shown in the lower portion of FIG. 51 as it would appear in flat configuration.

FIG. 52 is a cross-sectional view taken along lines 52-52 of FIG. 51.

FIG. 53 is a view taken along lines 53-53 of FIG. 51.

FIG. 53A is a view taken along lines 53A-53A of FIG. 53.

FIG. 54 is a top plan view of the patient dose selector knob of the patient dose selector subassembly of the fluid delivery device.

FIG. 55 is a view partly in cross-section taken along lines 55-55 of FIG. 54.

FIG. 56 is a view taken along lines 56-56 of FIG. 55.

FIG. 57 is a generally diagrammatic view illustrating the portion of the patient dose selector knob shown in the lower portion of FIG. 55 as it would appear in flat configuration.

FIG. 62 is a generally perspective, diagrammatic view illustrating the path of fluid flow through the device in a direction toward the bolus reservoir of the device.

FIG. 63 is a generally perspective, diagrammatic view illustrating the path of fluid flow outwardly of the bolus reservoir and toward the administration line of the device.

FIG. 78 is a cross-sectional view taken along lines 78-78 of FIG. 72.

FIG. 79 is a cross-sectional view taken along lines 79-79 of FIG. 78.

FIG. 80 is a cross-sectional view similar to FIG. 78, but showing the operating spring of the bolus plunger assembly in a compressed condition.

FIG. 81 is a cross-sectional view taken along lines 81-81 of FIG. 78.

FIG. 82 is a cross-sectional view taken along lines 82-82 of FIG. 78.

FIG. 83 is a top view of the secondary reservoir operating shaft of the bolus plunger assembly.

FIG. 84 is a cross-sectional view taken along lines 84-84 of FIG. 83.

FIG. 85 is a view taken along lines 85-85 of FIG. 84.

FIG. 86 is a view taken along lines 86-86 of FIG. 84.

FIGS. 87, 88 and 89 are generally perspective views of the bolus operating mechanism of the invention illustrating the sequential steps to be followed in operating the mechanism to accomplish the delivery to the patient of bolus doses.

DETAILED DESCRIPTION OF THE INVENTION

Definitions

As used herein the following terms have the following meanings:
Unitary Container A closed container formed from a single component.
Continuous/Uninterrupted Wall.

Figure 1:
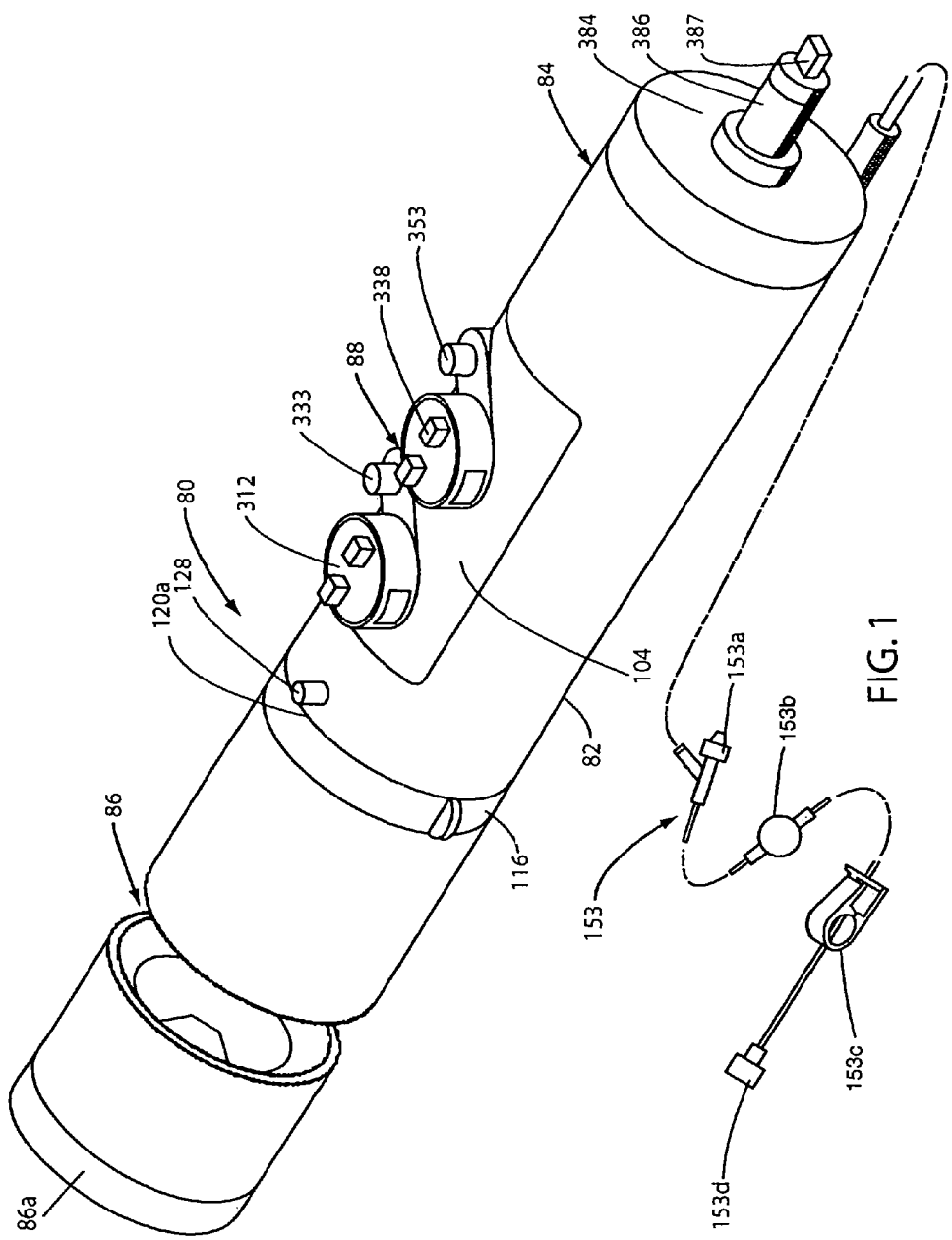
FIG. 1 is a generally perspective view of one form of the fluid dispensing device of the present invention for dispensing medicaments to a patient.
Figure 2:
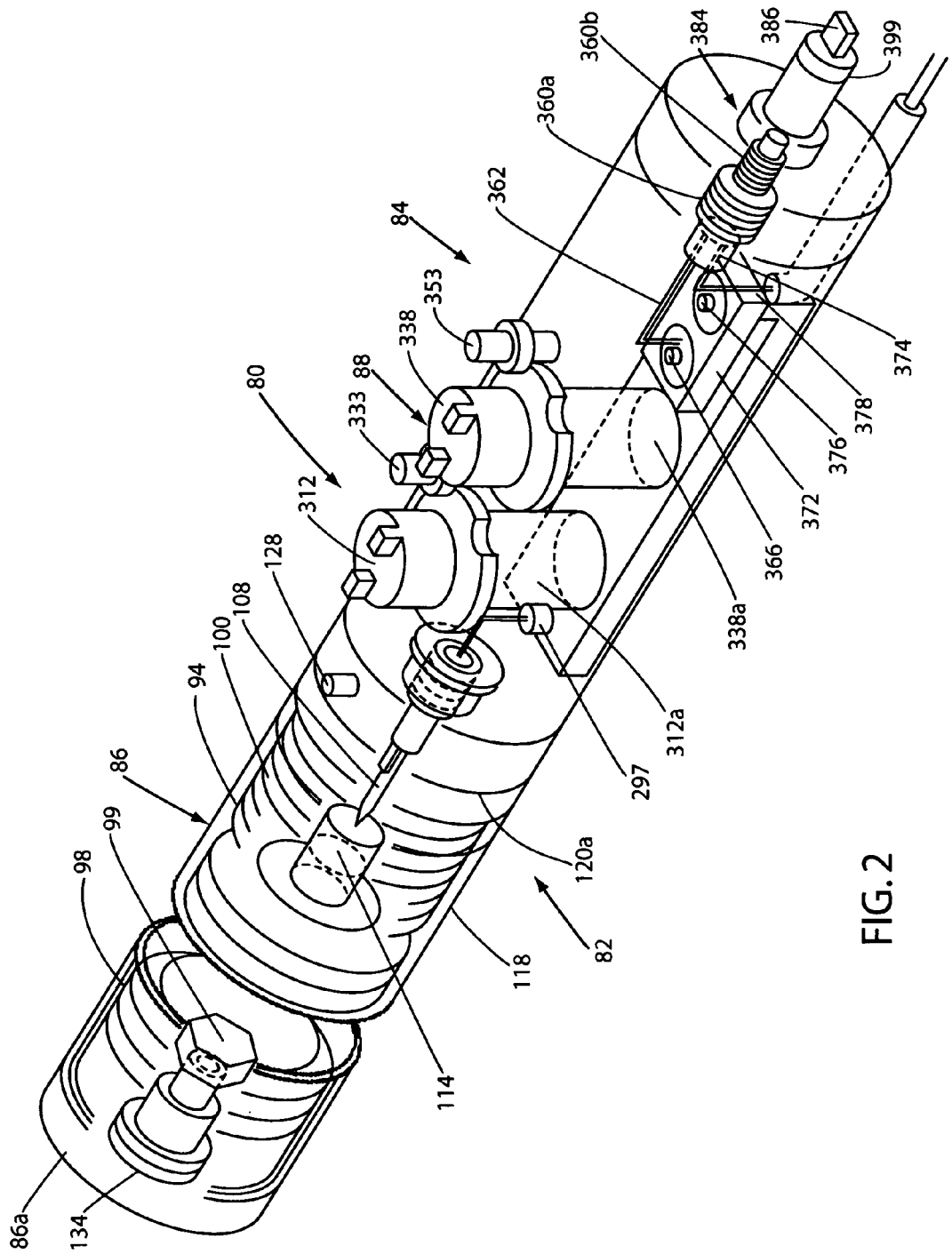
FIG. 2 is a generally perspective view of the fluid dispensing device shown in FIG. 1, but broken away to show internal construction.

A wall having no break in uniformity or continuity.
Hermetically Sealed Container A container that is designed and intended to be secure against the entry of microorganisms and to maintain the safety and quality of its contents after pressurizing.
Aseptic Processing The term 'aseptic processing' as it is applied in the pharmaceutical industry refers to the assembly of sterilized components and product in a specialized clean environment.
Sterile Product A sterile product is one that is free from all living organisms, whether in a vegetative or spore state.
Blow-Fill-Seal Process The concept of aseptic blow-fill-seal (BFS) is that a container is formed, filled, and sealed as a unitary container in a continuous manner without human intervention in a sterile enclosed area inside a machine. The process is multi-stepped, pharmaceutical grade resin is extruded into a tube, which is then formed into a container. A mandrel is inserted into the newly formed container and filled. The container is then sealed, all inside a sterile shrouded chamber. The product is then discharged to a non-sterile area for packaging and distribution.
Integrally Formed An article of one-piece construction or several parts that are rigidly secured together and is smoothly continuous in form and that any such components making up the part have been then rendered inseparable.
Frangible An article, item or object that is capable of being ruptured or broken, but does not necessarily imply any inherent materials weakness. A material object under load that demonstrates a mechanical strain rate deformation behavior, leading to disintegration.
Spring A mechanical element that can be deformed by a mechanical force such that the deformation is directly proportional to the force or torque applied to it. An elastic machine component able to deflect under load in a prescribed manner and to recover its initial shape when unloaded. The combination of force and displacement in a deflected spring is energy which may be stored when moving loads are being arrested.
Apparatus Of The Invention Referring to the drawings and particularly to FIGS. 1 and 2, one form of the fluid dispensing apparatus of the present invention for dispensing medicaments including sedatives such as propofol, dexmedetomidine hydrochloride and related compounds is there shown. This novel apparatus, which is generally designated in the drawings by the numeral 80, is particularly well suited for use in the sedation of initially intubated and mechanically ventilated patients during treatment in an intensive care unit. The apparatus here comprises a device housing 82 having a forward portion 84, a rear portion 86 having a base 86a and a central portion 88. Housing 82 can be constructed from metal, plastic or any suitable material.

Disposed within the rear portion 86 of the device housing is the important fluid delivery portion and disposed within the central portion 88 thereof is the novel fluid flow control means, which functions to control the flow of fluid from reservoir 94 (FIGS. 2 and 3) of the fluid delivery portion of the device toward the patient. Disposed within the forward portion 84 of the device housing is the bolus operating means of the invention which functions to permit selected bolus doses of medicaments to be delivered from reservoir 94 to the patient as may be required.

Considering first the fluid delivery portion of the fluid dispensing apparatus, this portion comprises a carriage 98 that carries and acts upon reservoir 94. Carriage 98 is movable between a first rearward position shown in FIG. 3 and a second advanced position shown in FIG. 5. As best seen by referring to FIGS. 3, 10 and 11 through 13, carriage 98 includes a carriage flange 98a and a reduced diameter portion 98b that receives the novel stored energy means of the present invention. Carriage 98 is releasably locked in its first position by a novel locking means the character of which will be described in the paragraphs which follow.

Figure 3:
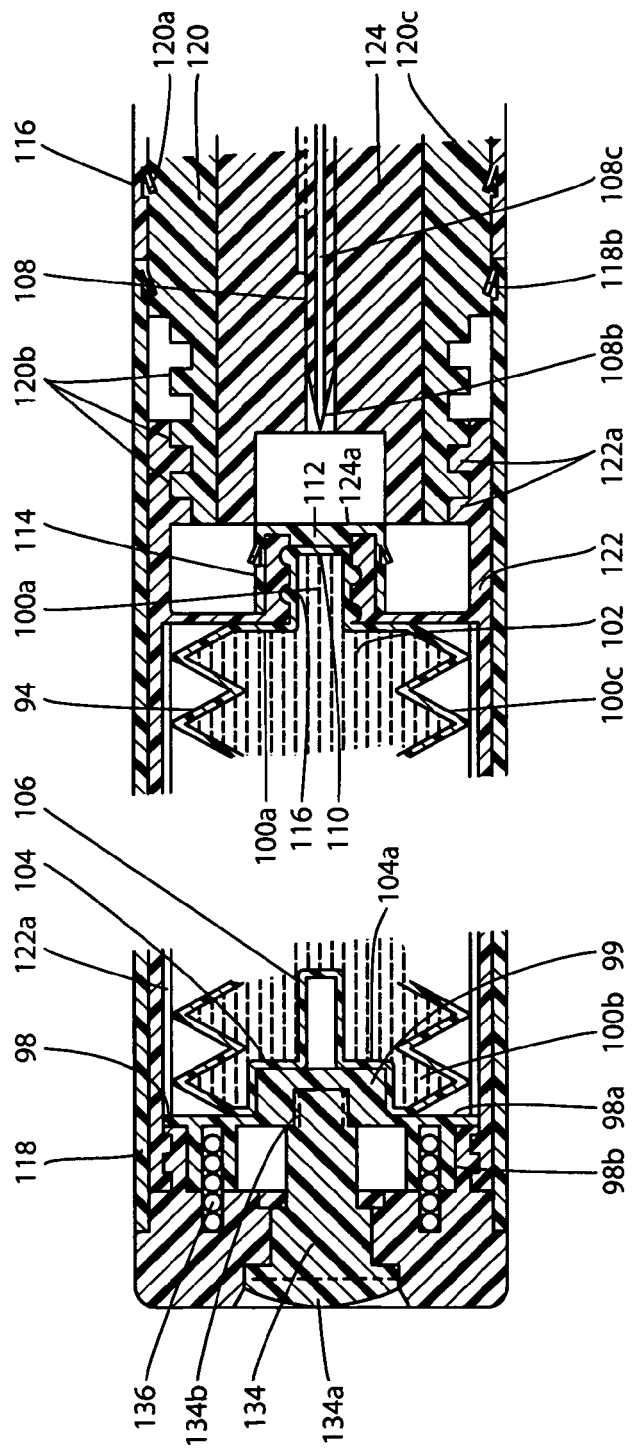
FIG. 3 is a longitudinal cross-sectional view of the rear, fluid delivery portion of the fluid dispensing device shown in FIG. 1.
Figure 15:
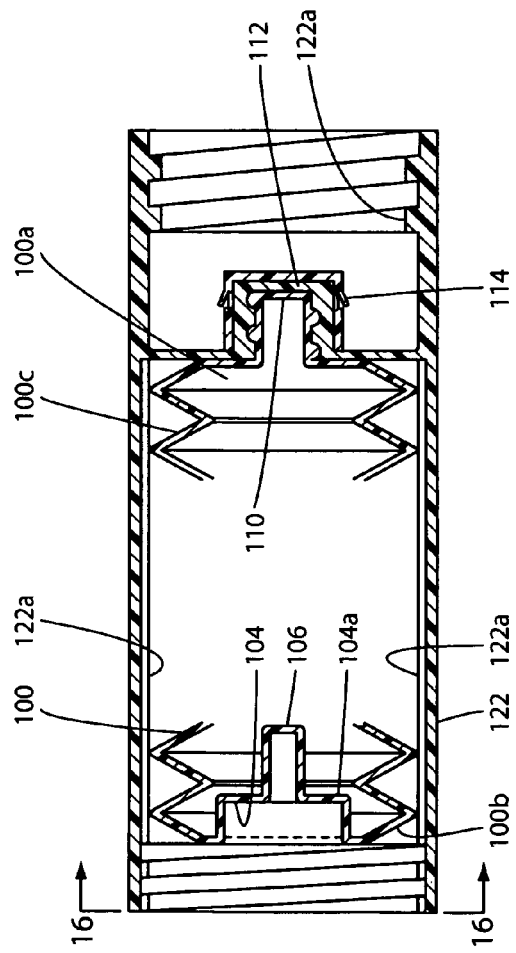
FIG. 15 is a cross-sectional view taken along lines 15-15 of FIG. 14.
Figure 16:
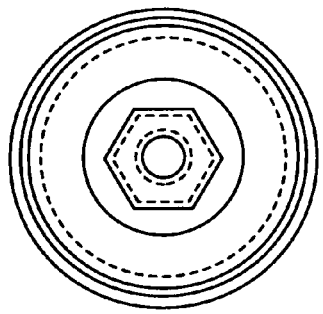
FIG. 16 is a view taken along lines 16-16 of FIG. 15.
Figure 17:
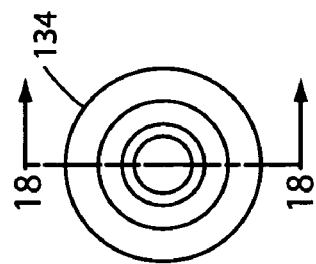
FIG. 17 is an enlarged, front view of the carriage release component of the fluid delivery portion of the fluid dispensing device.
Figure 18:
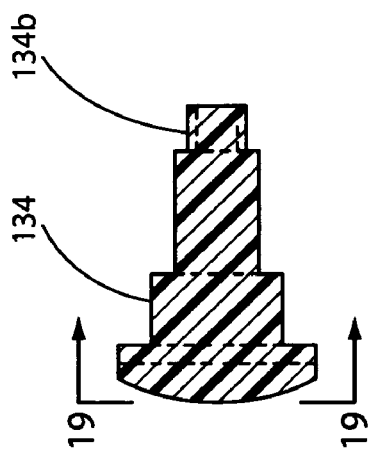
FIG. 18 is a cross-sectional view taken along lines 18-18 of FIG. 17.

Carried by carriage flange 98a, from which a generally hexagonal shaped protuberance 99 extends, is a reservoir defining assembly 100. Reservoir defining assembly 100 here comprises an integrally formed, hermetically sealed container, which as illustrated in FIGS. 3 and 15, includes a front portion 100a, a rear portion 100b and a collapsible accordion-like, continuous, uninterrupted side wall 100c that interconnects the front and rear portion of the assembly so as to define the fluid reservoir 102. As illustrated in the drawings, the accordion like side wall 100c comprises a multiplicity of adjacent generally "V" shaped interconnected folds, while rear portion 100b includes a generally cup shaped recess 104 having a wall 104a. As best seen in FIG. 3, hexagonal shaped protuberance 99 is closely received within the cup-shaped recess 104. Extending from wall 104a is an ullage defining protuberance 106, the purpose of which will presently be described.

Reservoir defining assembly 100 is constructed in accordance with aseptic blow-fill seal manufacturing techniques the character of which is well understood by those skilled in the art. Basically, this technique involves the continuous plastic extrusion through an extruder head of a length of parison in the form of a hollow tube between and through two co-acting first or main mold halves. The technique further includes the step of cutting off the parison below the extruder head and above the main mold halves to create an opening which allows a blowing and filling nozzle assembly to be moved downwardly into the opening in the parison for molding and then filling the molded container in a sterile fashion.

Containers for use in dispensing beneficial agents in specific dosages, such as the reservoir assembly of the present invention present unique requirements. For example, it is important that as much of the beneficial agents contained within the reservoir assembly be dispensed from a container to avoid improper dosage, waste and undue expense. Accordingly, the previously identified ullage defining protuberance 106 is provided, which functions to fill the interior space of the collapsible container when it is collapsed.

In a manner presently to be described, fluid medicament reservoir 102 of the reservoir defining assembly 100 is accessible via a penetrating member 108 that is adapted to pierce a closure wall 110 as well as a pierceable membrane 112 (FIGS. 3 and 15). Pierceable membrane 112 is positioned over closure wall 110 of by means of a closure cap 114 which is affixed to the neck portion 116 of reservoir defining assembly 100 (FIG. 15). As previously described, the reservoir defining assembly 100 is formed using the earlier described aseptic blow fill technique and the reservoir portion of the container is sealed by the thin closure wall 110. The piercable membrane 112 is then positioned over the closure wall and the internally threaded closure cap 114 is positioned over the piercable membrane and threadably secured to the externally threaded neck portion 116 in a conventional manner.

Figure 4:
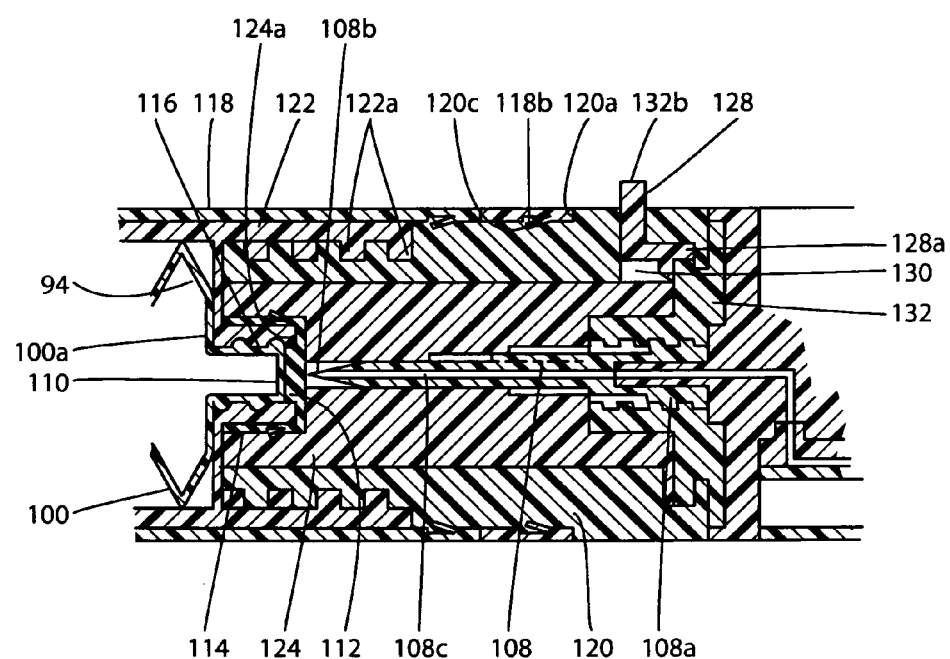
FIG. 4 is a foreshortened, longitudinal cross-sectional view similar to FIG. 3, but showing the advancement of the carriage and fluid reservoir components of the fluid dispensing device.

The first step in using the apparatus of the invention, is to remove the tear off spacer 116 that is disposed between the reservoir outer shell 118 and a shoulder 120a provided on the reservoir connector housing 120 of the apparatus (FIG. 3). Tear off spacer 116 functions to prevent the threadable advancement of the reservoir advancement housing 122 from the position shown in FIG. 3 of the drawings to the position shown in FIG. 4. Once the tear off spacer is removed, rotation of the reservoir outer shell 118 will cause the threads 122a formed on the reservoir advancement housing 122 to advance over the threads 120b formed on the reservoir connector housing 120 (see FIG. 4). As the assemblage made up of the reservoir outer shell 118 and the reservoir advancement housing 122 is advanced as the assemblage is rotated, a locking tab 118b formed on the reservoir outer shell 118 will move into locking engagement with a locking groove 120c formed in the reservoir connector housing 120. In this way, the reservoir connector housing 120 is interconnected with the assembly made up of the reservoir outer shell 118 and the reservoir advancement housing 122 so that rotation of the reservoir outer shell 118 will cause advancement of the pierceable member 108.

Figure 5:
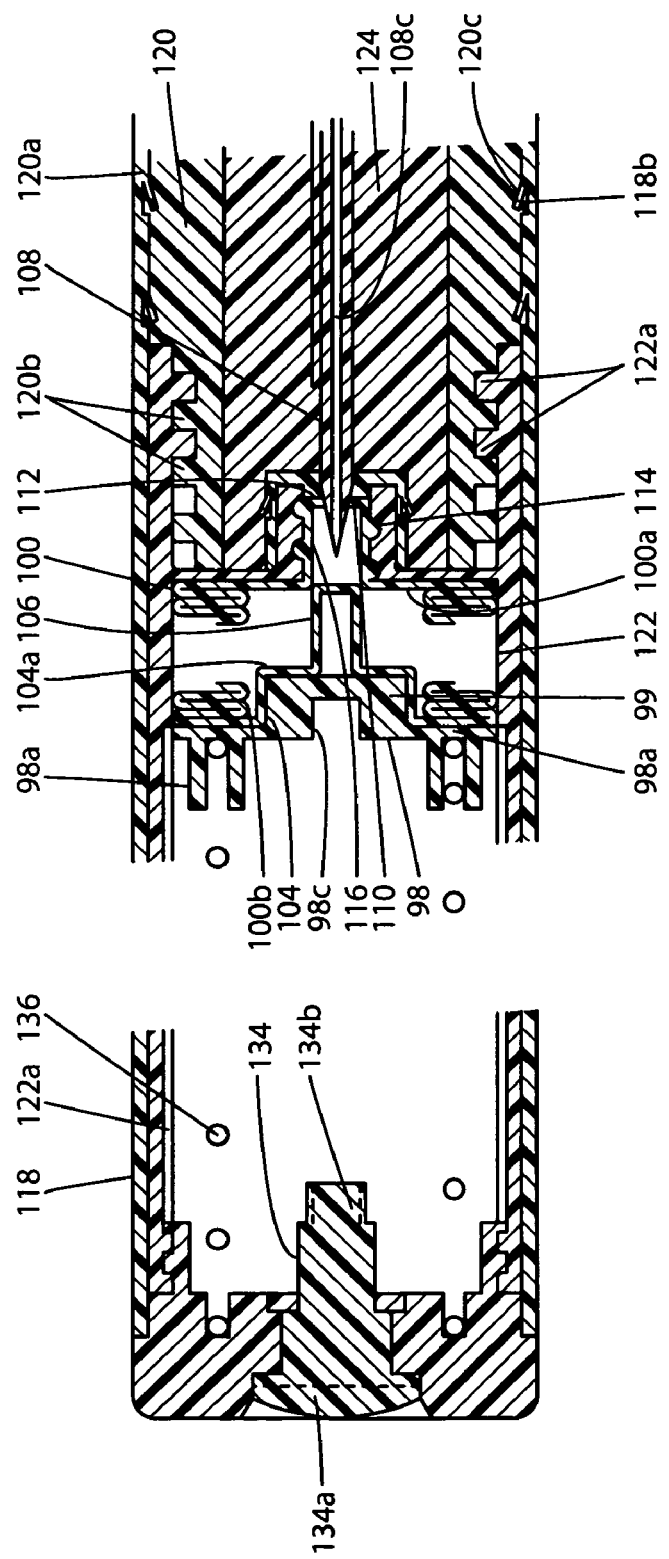
FIG. 5 is an enlarged, fragmentary cross-sectional view similar to FIGS. 3 and 4, but showing the advancement of the carriage by the stored energy means of the invention in a manner to collapse the side walls of the reservoir defining assembly.
Figure 9:
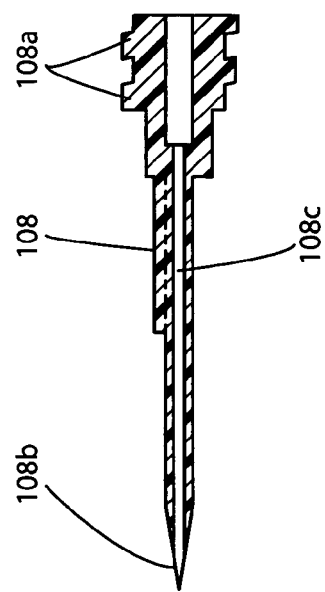
FIG. 9 is an enlarged, cross-sectional view of the penetrating member.
Figure 8:
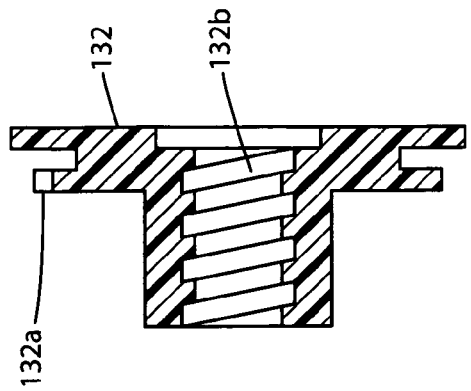
FIG. 8 is an enlarged, fragmentary cross-sectional view of the penetrating member housing of the fluid flow actuation subsystem.
Figure 7:
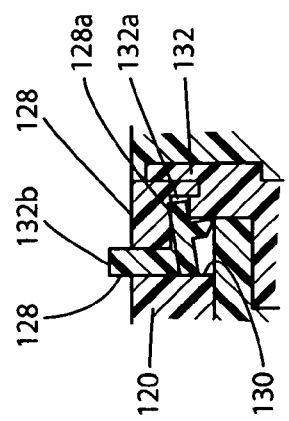
FIG. 7 is an enlarged, fragmentary cross-sectional view similar to FIG. 6, but showing the fluid flow actuation locking device in a release configuration permitting rotation of the reservoir housing to advance the penetrating member of the fluid flow actuation subsystem.
Figure 6:
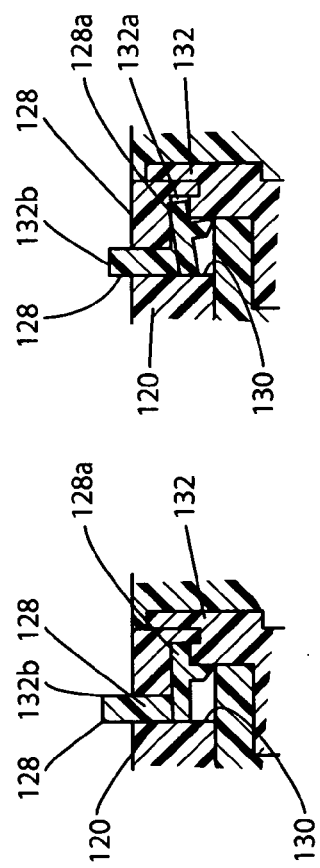
FIG. 6 is an enlarged, fragmentary cross-sectional view of the fluid flow actuation locking device portion of the fluid flow actuation subsystem.

It is to be observed that as the assemblage made up of the reservoir outer shell 118 and the reservoir advancement housing 122 is advanced, the neck portion 114 of the reservoir defining assembly 100 moves from the position shown in FIG. 3 to the position shown in FIG. 5 wherein it resides within a cavity 124a formed in the bearing shaft 124. With the neck portion 114 of the reservoir defining assembly 100 in position within cavity 124a, the fluid delivery step can commence by rotating the entire rearward portion of the housing. However, in order to enable this rotation, the locking means, or locking member 128 must be manipulated in the manner illustrated in FIGS. 6 and 7 of the drawings. As best seen in FIGS. 6 and 7, locking member 128, which is received within a cavity 130 formed in reservoir connector housing 120, includes a locking finger 128a that is received within a cavity 132a (FIG. 7) that is formed within a mounting block 132 (see also FIG. 8). Locking member 128 also includes an outwardly extending, finger engaging plunger 132b. As indicated in FIG. 7, a downward pressure exerted on the finger engaging plunger 132b will yieldably deform the lower portion of the locking member in a manner to move locking finger 128 out of cavity 132a in the manner shown in FIG. 7, thereby permitting rotation of the rearward portion of the housing along with the mounting block 132. As the mounting block 132 rotates, the internal threads 132b formed on the mounting block will engage the external threads 108a formed on the penetrating member (FIG. 9) causing the penetrating member to advance into the position shown in FIG. 5. As the penetrating member advances, the piercing point 108b of the penetrating member will first pierce the elastomeric member 112 and will then pierce closure wall 110 (see also FIG. 15) so as to open communication between the fluid reservoir 102 and the internal passageway 108c of the penetrating member.

Figure 10:
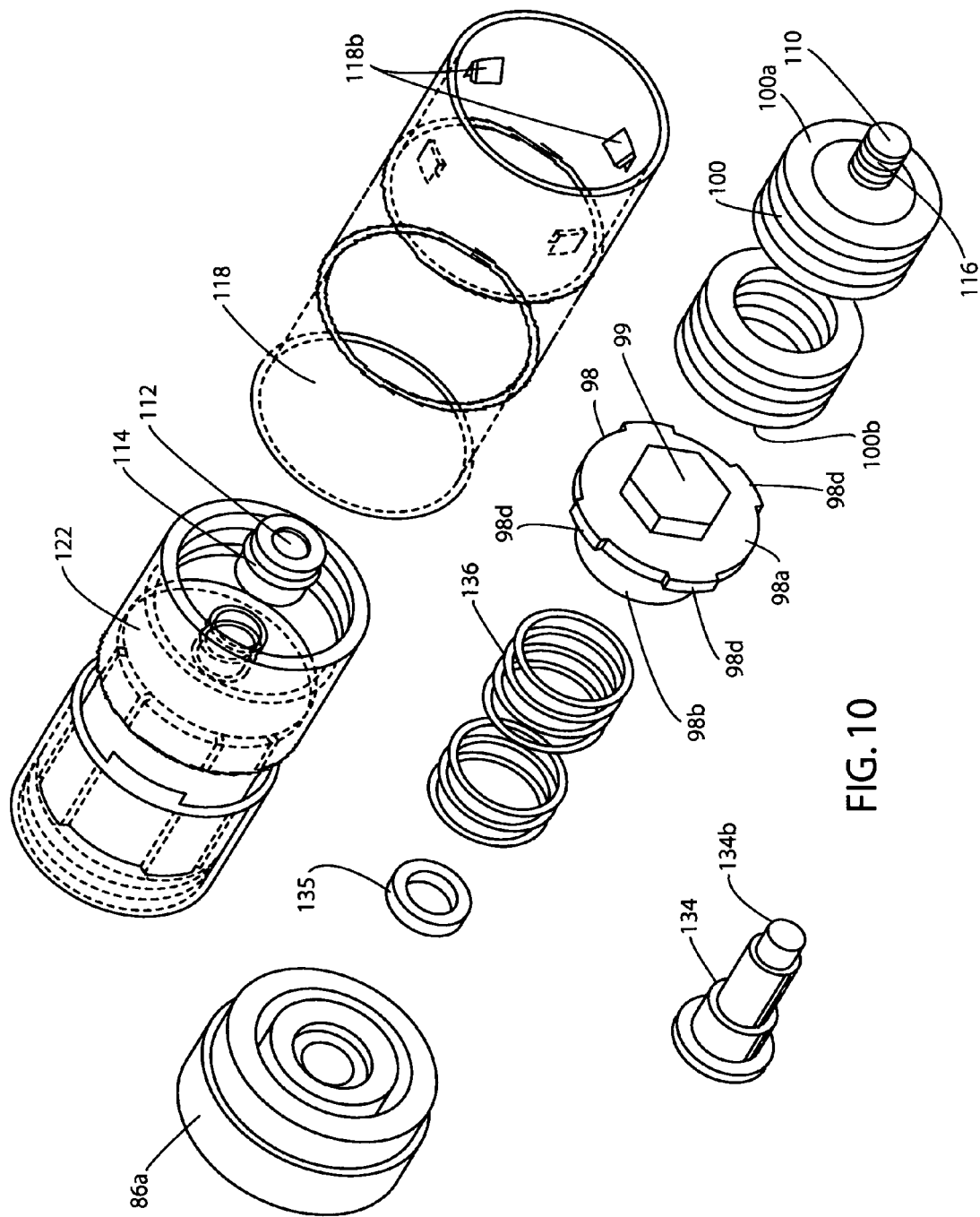
FIG. 10 is a generally perspective, exploded view of the rear, fluid delivery portion of the fluid dispensing device shown in FIG. 1
Figure 11:
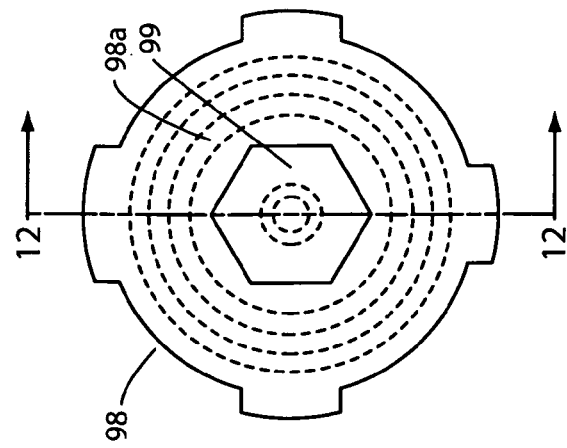
FIG. 11 is an enlarged front view of the reservoir carriage of the fluid flow actuation subsystem.
Figure 12:
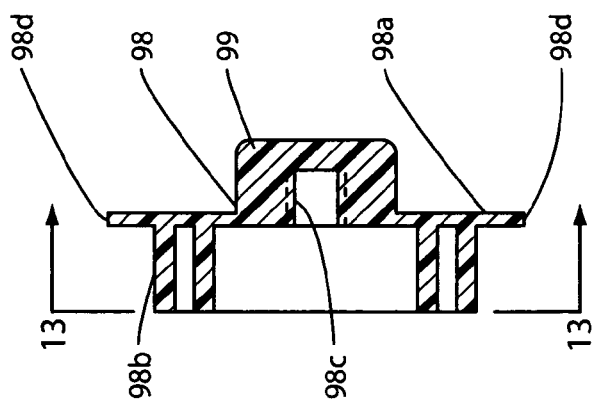
FIG. 12 is a cross-sectional view taken along lines 12-12 of FIG. 11.
Figure 13:
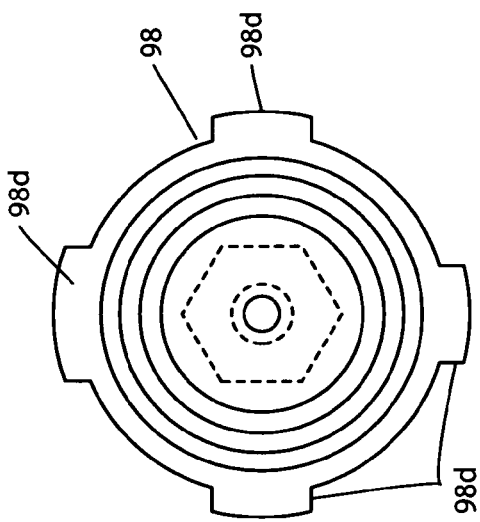
FIG. 13 is a view taken along lines 13-13 of FIG. 12.
Figure 14:
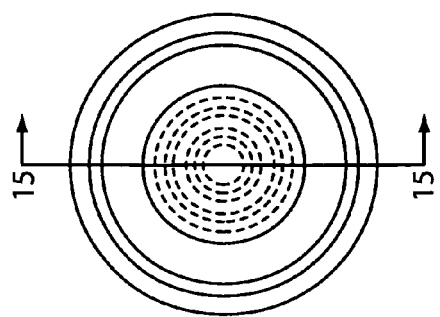
FIG. 14 is an enlarged, front view of the reservoir and advancement housing subassembly of the fluid delivery portion of the fluid dispensing device shown in FIG. 1.
Figure 19:
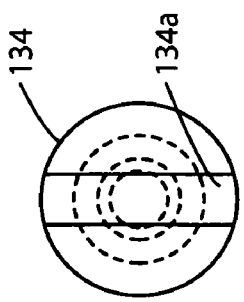
FIG. 19 is a view taken along lines 19-19 of FIG. 18.

With communication between the fluid reservoir and the internal passageway of the penetrating member having been established in the manner thusly described, the fluid contained within the fluid reservoir can be expelled by rotating the carriage release knob 134, which is held within base portion 86a by a retaining ring 135 (FIG. 10). This is accomplished by grasping the finger engaging rib 134a (FIG. 19) and rotating the knob until the threaded end 134b is free from the internally threaded cavity 98c formed in the carriage 98 (FIG. 5). Once the carriage release knob is freed from the carriage, the stored energy source, here shown as a coil spring 136 that is movable from the first compressed position shown in FIG. 3 to a second extended position shown in FIG. 5, will urge the carriage forwardly in the manner illustrated in FIG. 5 of the drawings. As the carriage moves forwardly the circumferentially spaced guide tabs 98d formed on the carriage will slide within and be guided by guide channels 122g formed in reservoir advancement housing 122. As the accordion side walls collapse, the fluid will be forced outwardly of the reservoir into internal passageway 108c of the penetrating member. In a manner presently to be described, the fluid will then flow toward the fluid flow control means of the invention, which functions to control the flow of fluid from the fluid reservoir of the fluid delivery portion of the device toward the patient.

The fluid flow control means, which is carried by the central portion 88 of the housing, here comprises dose control means for controlling the dose of medicament to be delivered to the patient and rate control means for controlling the rate of medicament flow from collapsible reservoir toward the dose control means.

Figure 42:
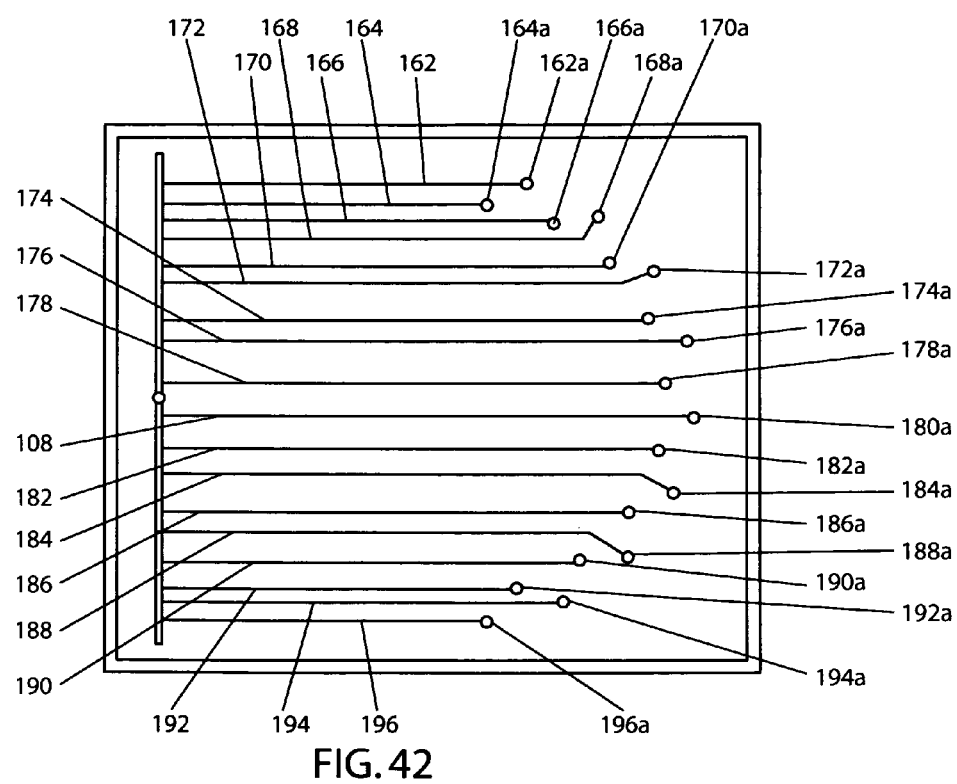
FIG. 42 is a top plan view of the bottom rate control plate of the fluid delivery device illustrated in FIG. 25.
Figure 47:
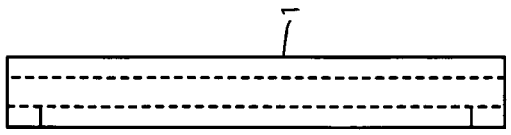
FIG. 47 is a view taken along lines 47-47 of FIG. 43.
Figure 45:
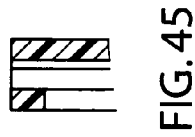
FIG. 45 is a cross-sectional view taken along lines 45-45 of FIG. 43.
Figure 43:
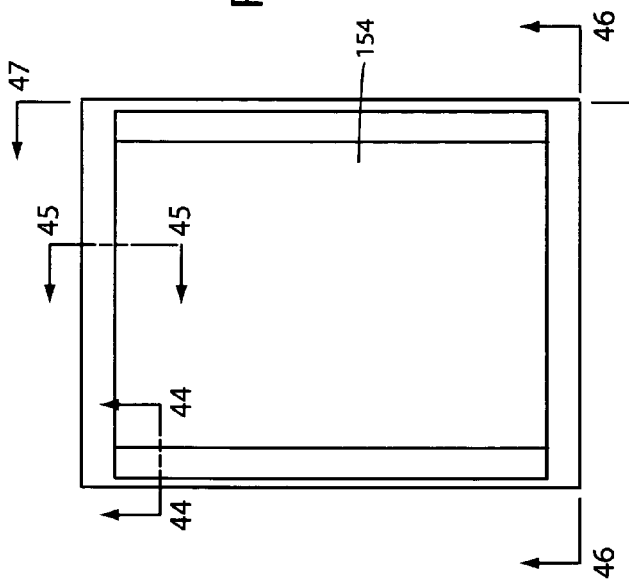
FIG. 43 is a top elevation view of the rate control assembly retaining cover of the fluid delivery device.
Figure 46:
FIG. 46 is a view taken along lines 46-46 of FIG. 43.
Figure 44:
FIG. 44 is a cross-sectional view taken along lines 44-44 of FIG. 43.
Figure 49:
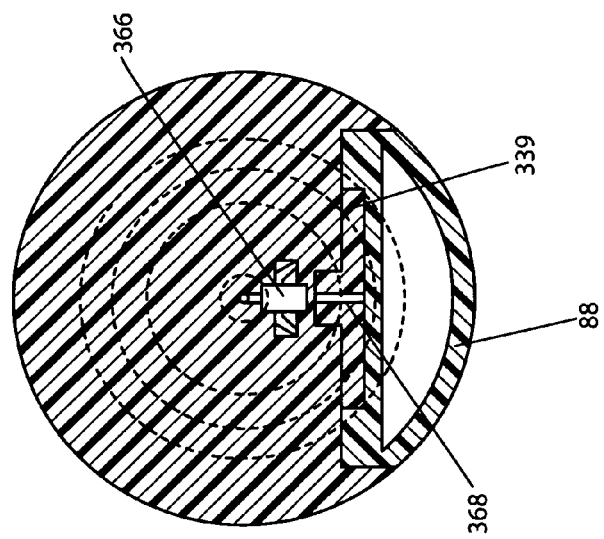
FIG. 49 is a view taken along lines 49-49 of FIG. 21B.

Considering first the rate control component of the fluid flow control means, as best seen in FIGS. 21 through 51, this novel means here comprises a flow rate control assembly 156 (FIGS. 24 and 25) for controlling the rate of fluid flow toward the dose control means. Flow rate control assembly 156 includes a first, or lower rate control plate 158 and a second, or upper, rate control plate 160 (FIGS. 24, 25, 39, 40 and 42). As best seen in FIG. 42, the bottom side of rate control plate 160 is uniquely provided with a plurality of fluidic micro-channels identified in the drawings as 162, 164, 166, 168, 170, 172, 174, 176, 178, 180, 182, 184, 186, 188, 190, 192, 194 and 196. Each of the fluidic micro-channels is also provided with an outlet 162a, 164a, 166a, 168a, 170a, 172a, 174a, 176a, 178a, 180a, 182a, 184a, 186a, 188a, 190a, 192a, 194a and 196a, respectively.

Figure 39:
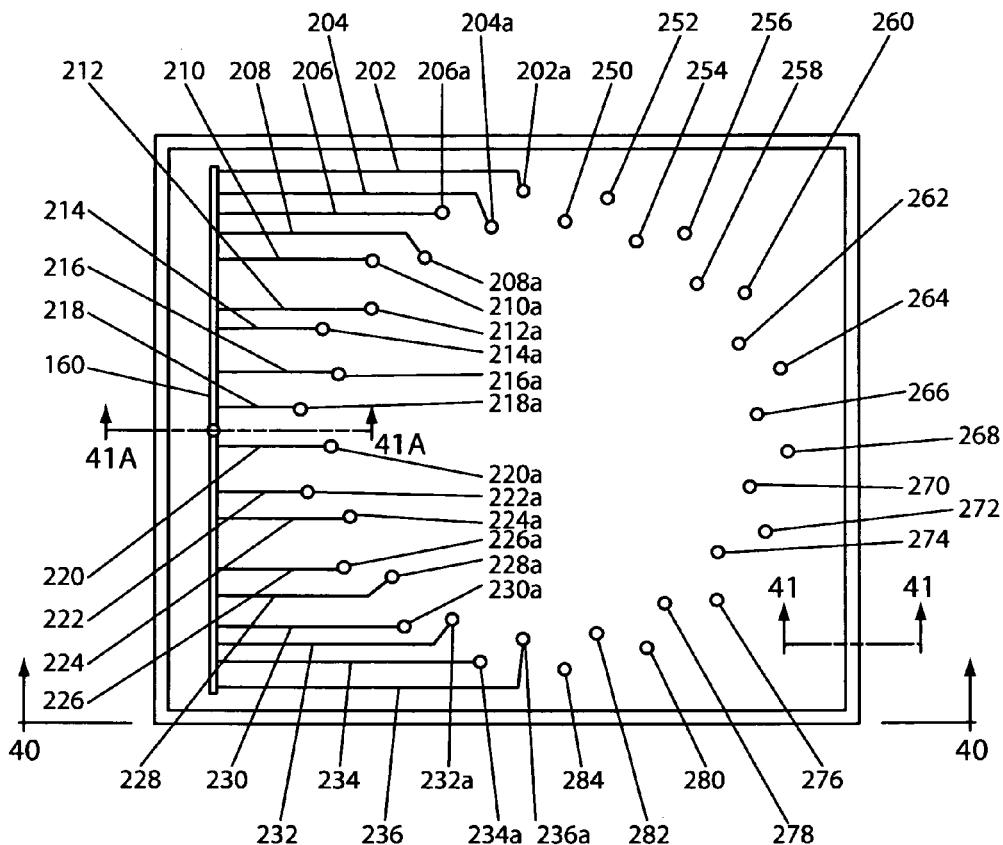
FIG. 39 is a top plan view of the rate control plate of the fluid delivery device illustrated in FIG. 25.
Figure 41:
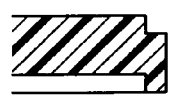
FIG. 41 is a view taken along lines 41-41 of FIG. 39.
Figure 40:
FIG. 40 is a cross-sectional view taken along lines 40-40 of FIG. 39.

As best seen in FIG. 39, upper side of rate control plate 160 is also uniquely provided with a plurality of fluidic micro-channels of different lengths that are identified in the drawings as 202, 204, 206, 208, 210, 212, 214, 216, 218, 220, 222, 224, 226, 228, 230, 232, 234 and 236. Each of the fluidic micro-channels is also provided with an outlet 202a, 204a, 206a, 208a, 210a, 212a, 214a, 216a, 218a, 220a, 222a, 224a, 226a, 228a, 230a, 232a, 234a and 236a, respectively. Upper control plate 160 is also provided with inlet ports 250, 252, 254, 256, 258, 260, 262, 264, 266, 268, 270, 272, 274, 276, 278, 280, 282 and 284 that communicate with the outlet ports 162a through 196a of lower side of control plate 160.

Figure 23:
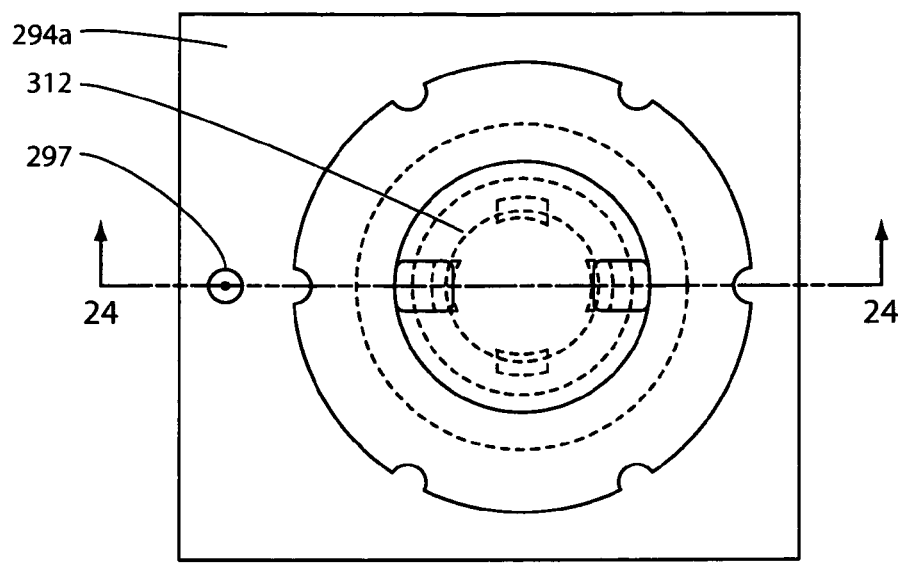
FIG. 23 is an enlarged top plan view of the patient weight selector subassembly of the fluid dispensing device.
Figure 24:
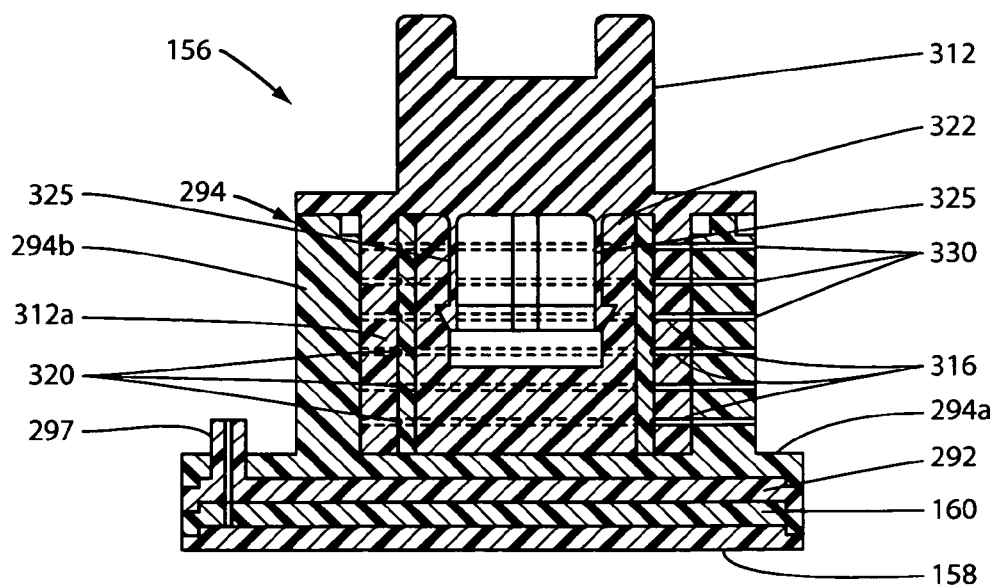
FIG. 24 is a cross-sectional view taken along lines 24-24 of FIG. 23.
Figure 25:
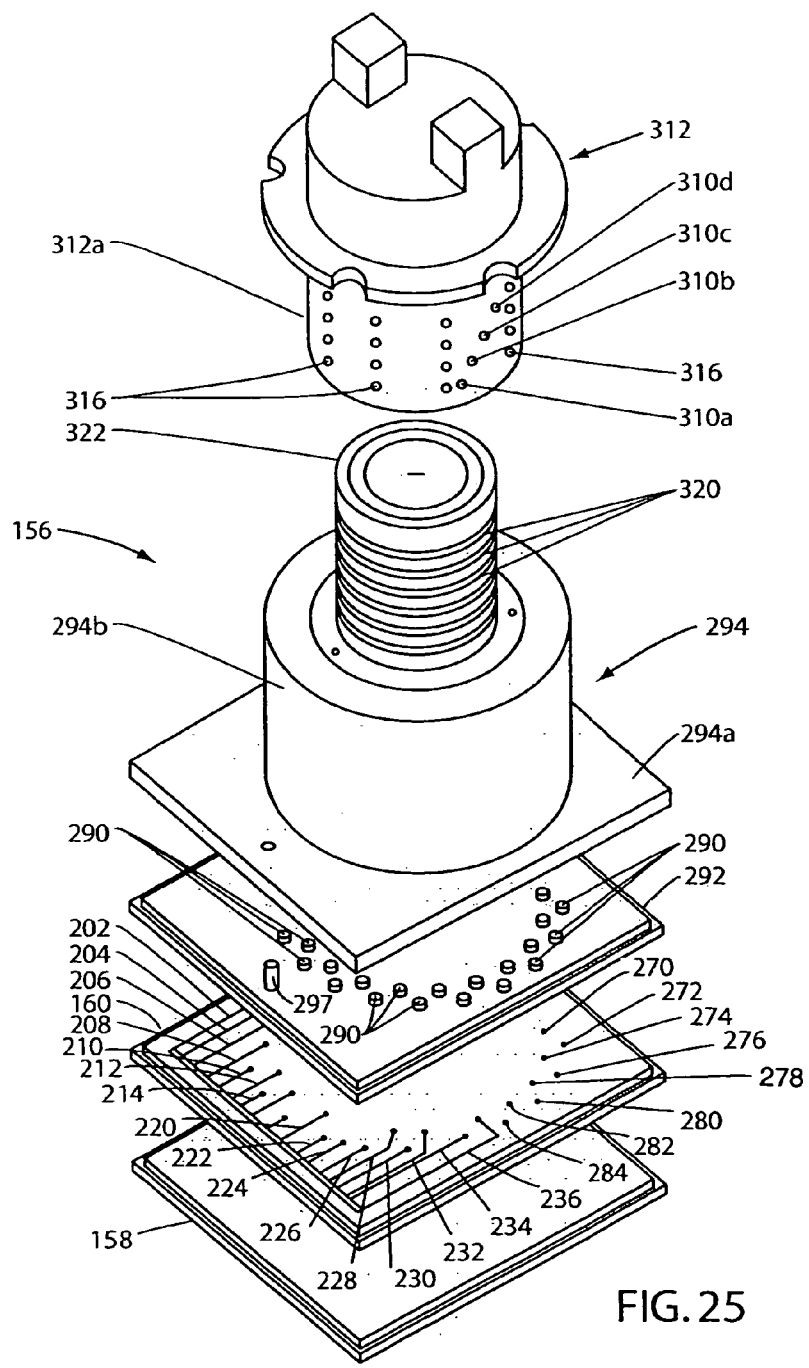
FIG. 25 is an enlarged, generally perspective exploded view of the patient weight selector subassembly of the fluid dispensing device.

As best seen in FIG. 25, the inlet ports of the upper control plate as well as the outlet ports thereof communicate with a multiplicity of spaced apart fluid ports 290 formed in rate control distribution plate 292. From fluid ports 290, the fluid flows toward the novel fluid pickup housing 294 of the invention. As illustrated in FIGS. 23 and 24, fluid pickup housing 294 includes a base 294a and tower portion 294b that is provided with a multiplicity of circumferentially spaced apart, generally vertically extending fluid passageways 296 of varying lengths.

Figure 27:
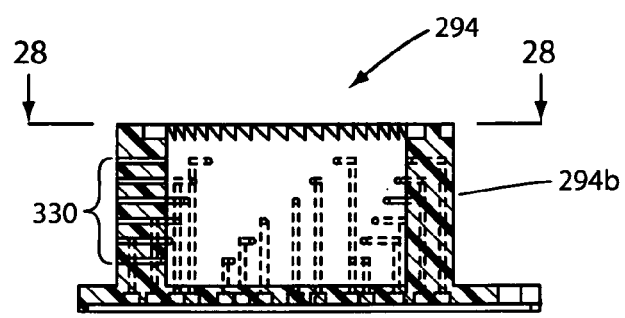
FIG. 27 is a cross-sectional view taken along lines 27-27 of FIG. 26 showing the main fluid pickup housing device in greater detail.
Figure 26:
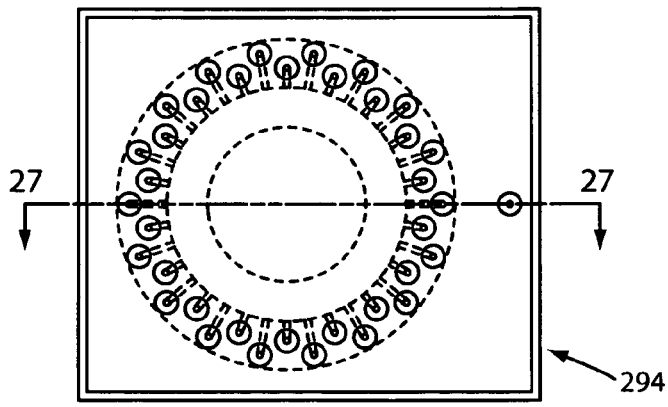
FIG. 26 is a bottom plan view of the upper rate control plate of the patient weight selector subassembly illustrated in FIG. 25 and showing in phantom lines the main fluid pickup housing of the device.
Figure 31:
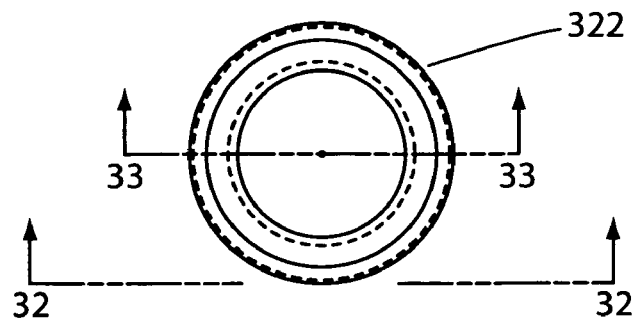
FIG. 31 is a top plan view of the fluid connector boss of the fluid delivery device illustrated in FIG. 25.
Figure 32:
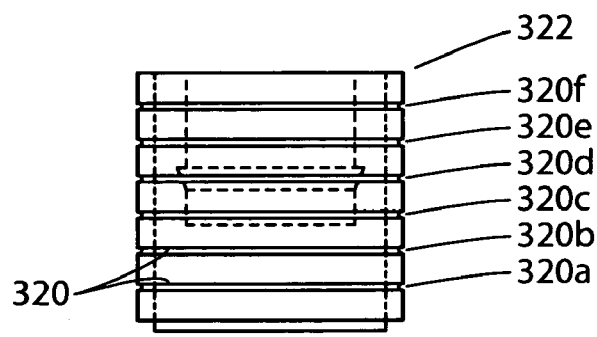
FIG. 32 is a side elevation view of the fluid connector boss shown in FIG. 31 illustrating the configuration of the fluid micro pickup of the connector boss.
Figure 33:
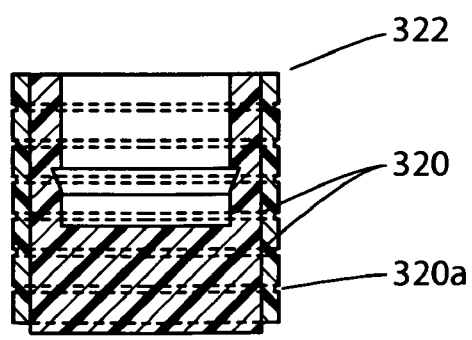
FIG. 33 is a cross sectional view taken along lines 33-33 of FIG. 31.
Figure 41A:
FIG. 41A is a view taken along lines 41A-41A of FIG. 39.

With the construction described in the preceding paragraphs, fluid flowing from the fluid reservoir will fill fluidic micro channels 162 through 196 as well as fluidic micro channels 202 through 236 via an inlet port 297 carried by rate control distribution plate 292 (see FIGS. 25 and 34). Fluid flowing through the outlet ports of these fluidic micro-channels will flow into spaced apart fluid ports 290 formed in rate control distribution plate 292. From fluid ports 290, the fluid will flow into and fill the circumferentially spaced apart, generally vertically extending fluid passageways 296 of fluid pickup housing 294 (FIGS. 26, 27, 28 and 29). Referring to FIG. 30, which is a depiction of the inner surface of fluid pickup housing 294 when viewed in a planar configuration, it is to be noted that fluid passageways 296 are arranged in six spaced part groups of passageways 298, 300, 302, 304, 306 and 308 respectively. Each group of passageways is made up of six spaced apart passageways of a different length, each passageway having an outlet located at a different height with respect to base 294*a* of the fluid pick-up housing (FIG. 27). From a selected one of the six groups of fluid passageways 296, the fluid will flow into a group of six vertically and circumferentially spaced apart inlets 310 (FIGS. 53 and 53A) formed in the skirt portion 312*a* of a patient weight selector knob 312 (see also FIG. 30, which is a depiction of the inner surface of the skirt portion when viewed in a planar configuration). For a purpose presently to be described, the skirt portion 312*a* of patient weight selector knob 312 is also provided with six circumferentially spaced apart outlet groups 314, each group having six vertically spaced apart outlet ports 316. From inlets 310, the fluid will flow into a plurality of vertically spaced apart, circumferentially extending fluid passageways 320 formed in a fluid pickup housing 322 (FIGS. 28, 29 and 30) that is housed interiorly of the downwardly depending skirt 312*a* of the patient weight selector knob 312 (see FIGS. 21B, 22, and 23). Retaining tabs 325 are disposed interiorly of skirt 312*a* (FIG. 51). The fluid pickup housing 322 is bonded to pickup housing 294, forming a rigid support to snap the retaining tabs 325 into pickup housing 322.

With the construction described in the preceding paragraphs, fluid flowing from the fluid reservoir will fill fluidic micro channels 162 through 196 (FIG. 42) as well as fluidic micro channels 202 through 236 (FIG. 39), will fill the fluid passageways 296 of fluid pickup housing 294 (FIG. 27) and will fill the circumferentially extending fluid passageways 320 formed in a fluid pickup housing 322 (FIG. 25). From fluid passageways 320 the fluid will flow into the vertically spaced apart outlet passageways 316 formed in patient weight selector knob 312 (FIG. 24).

When the patient weight selector knob 312 is rotated into the position shown in FIG. 24, fluid will flow from outlet ports 316 into the six vertically spaced apart, transversely extending fluid passageways 330 formed in fluid pickup housing 294. As will presently be described, fluid passageways 330 communicate with the dose control means of the invention which, as previously mentioned, functions to control the dose of medicament to be delivered to the patient.

Figure 21A:
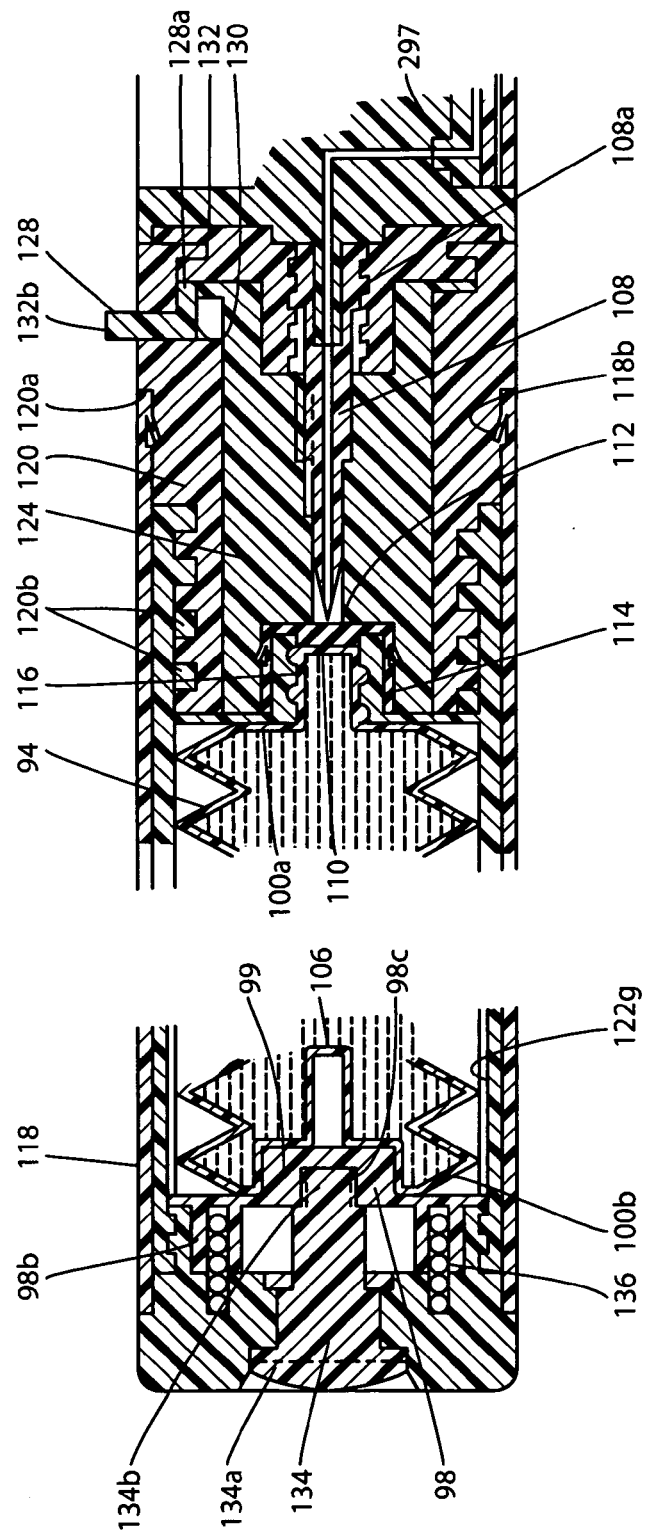
FIGS. 21A and 21B when considered together comprise an enlarged, longitudinal cross-sectional view of the fluid dispensing device shown in FIG. 2.
Figure 21B:
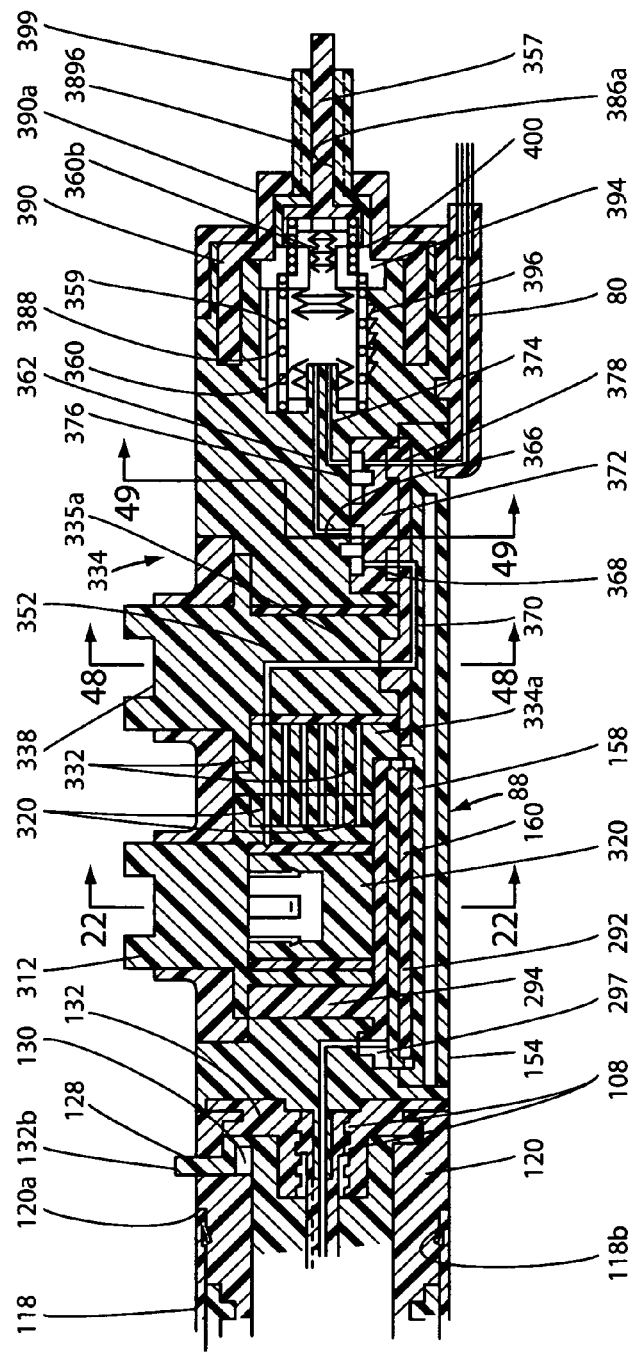
Figure 22:
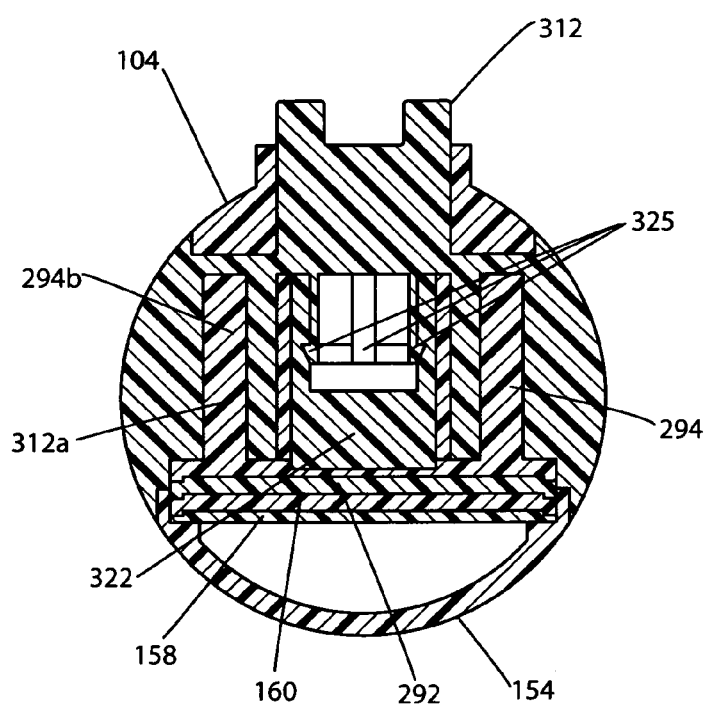
FIG. 22 is a cross-sectional view taken along lines 22-22 of FIG. 21B.

With the patient weight selector knob 312 in position (FIG. 24) wherein inlets 310 (FIG. 53A) align with one of the groups 298 through 308 (FIG. 30) of fluid passageways 296, fluid will flow from the fluid reservoir through inlet 297 (FIG. 25) into the fluidic micro-channels of different lengths formed in upper and lower surfaces of lower rate control plate 160 (FIGS. 39 and 42), into vertically extending fluid passageways 296 of fluid pickup housing 294 (FIG. 27), into inlets 310 (FIG. 25), into passageways 320 formed in the fluid pickup assembly 322, into passageways 316 of the patient weight selector knob 312, into passageways 330 of the fluid pickup assembly 294 and finally into passageways 332 of body portion 334*a* of the dose control assembly 334. It is apparent that the rate of fluid flow toward the dose control means depends upon the configuration of the rate control passageways formed in the rate control plate 160 that are in communication with inlets 310 via vertically extending fluid passageways 296. By way of example, assume that the patient weight selector knob 312 is rotated into a position wherein inlets 310*a*, 310*b*, 310*c*, 310*d*, 310*e* and 310*f* (FIG. 51A) align with the passageways 296*a*, 296*b*, 296*c*, 296*d*, 296*e* and 296*f* of group 298 (FIG. 30). Assume further, that the six passageways 296*a*, 296*b*, 296*c*, 296*d*, 296*e* and 296*f* are in communication with fluid passageways 162, 164, 166, 168, 170 and 172 respectively of rate control plane 160 (FIG. 42). In this situation, fluid will flow from fluid passageway 162 into passageway 296*a*, then into passageway 310*a* and finally into the lower most circumferentially extending passageway 320*a* formed in the fluid pickup assembly 322 (FIG. 21B). Similarly, in this situation, fluid will flow from fluid passageway 164 into passageway 296*b*, then into passageway 310*b* and finally into circumferentially extending passageway 320*b* formed in the fluid pickup assembly 322 (FIG. 24). The fluid will flow in a similar manner from passageways 166, 168, 170 and 172 into the remaining circumferentially extending passageway 320 formed in the fluid pickup assembly 322.

Figure 58:
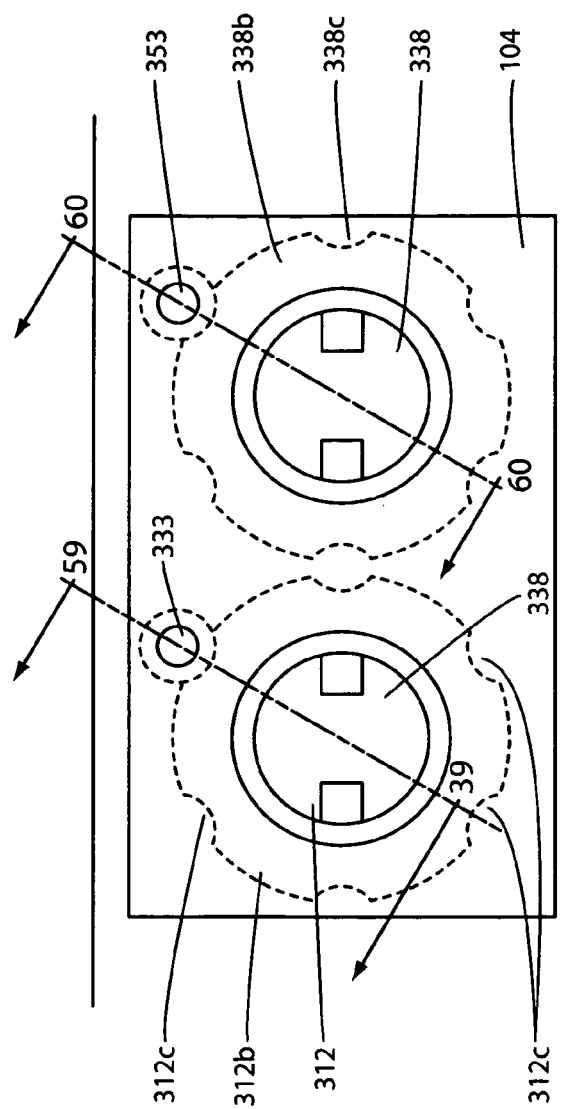
FIG. 58 is a top plan view of the patient weight selector knob and the patient dose selector knob components of the fluid dispensing device.
Figure 59:
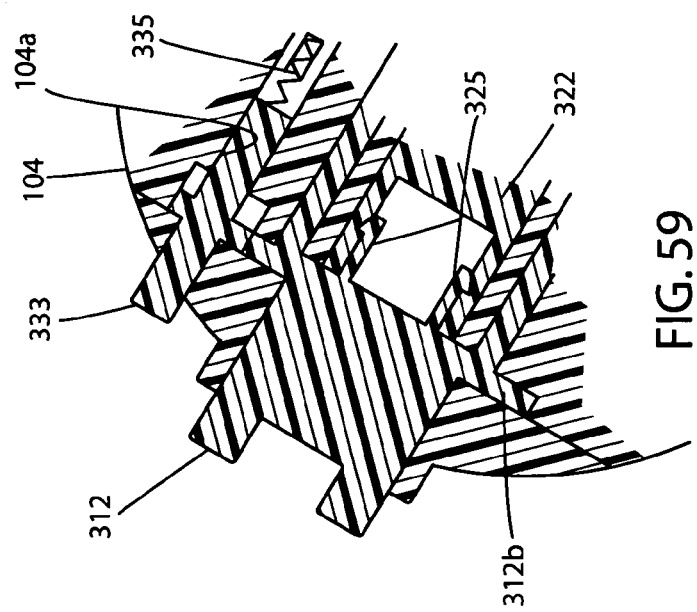
FIG. 59 is a cross-sectional view taken along lines 59-59 of FIG. 58.

As illustrated in FIGS. 58 and 59 of the drawings, rate control indexing means are provided to position the locking knob 312 in a selected rotational position. In the present form of the invention, this rate control indexing means comprises a locking plunger 333 that is received within a bore 104*a* formed in the forward portion 104 of housing 102. Locking plunger 333 is continuously biased outwardly by a coiled spring 335 into locking engagement with a selected one of a plurality of circumferentially spaced apart cutouts 312*c* formed in the flange portion 312*b* of the locking knob assembly 312. With this construction, in order to rotate the locking knob from the selected rotational position, the locking plunger 333 must be manually pushed inwardly against the urging of spring 335.

Figure 48:
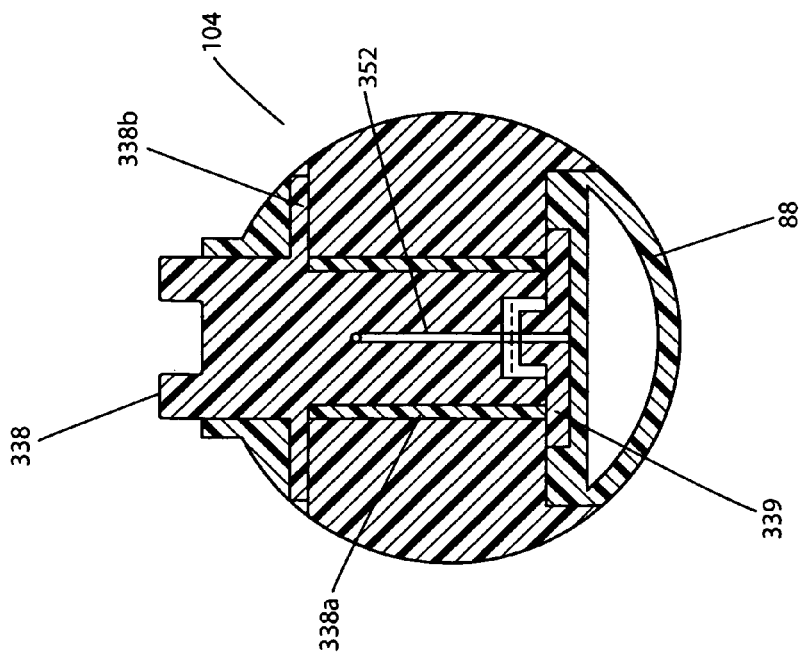
FIG. 48 is a view taken along lines 48-48 of FIG. 21B.

Turning now particularly to FIGS. 21B and 54 through 56, rotatably mounted within body portion 334*a* of the dose control assembly 334 is the patient dose selector knob 338 and formed within a body portion 338*a* of the dose selector knob vertically spaced-apart radially outwardly extending fluid passageways 340, 342, 344, 346, 348 and 350 (FIGS. 55, 56 and 57). As shown in FIG. 48, dose selector knob 338 rests on a base support 339. By rotating the dose selector knob within body portion 334*a*, the radially outwardly extending fluid passageways can be selectively brought in to communication with the passageways 332 that are, in turn, in communication with the circumferentially extending passageway 320 formed in the fluid pickup assembly 322 of the rate control means of the invention. By way of example, in FIG. 21 of the drawings radially outwardly extending fluid passageway 340 is shown in communication with the uppermost passageway 332 of the dose control means.

As illustrated in FIG. 55, each of the radially outwardly extending fluid passageways is in communication with an axially extending passageway 352 that is, in turn, in communication with the bolus operating mechanism of the invention, the character of which will presently be described.

By way of example, further rotation of the dose selector knob within body portion 334*a* can bring radially outwardly extending fluid passageway 350 into communication with circumferentially extending passageway 320*a* of fluid pickup assembly 322 via the lower-most passageway 332. In this situation, it can be seen that fluid passageway 350 is in communication with fluid passageway 162 of the lower surface of rate control plate 160 via the lower most passageway 332, the lower most passageway 330, the lower most passageway 316, circumferentially extending passageway 320a and passageway 296a. Similarly, in this example, by controlled rotation of the dose selector knob, each of the fluid passageways formed in the dose selector knob can be brought into communication with a selected one of the passageways 164 through 172 formed in the rate control plate 160. In this way, the rate of fluid flow toward the patient of the medicinal fluid contained within the device reservoir can be closely controlled.

Figure 60:
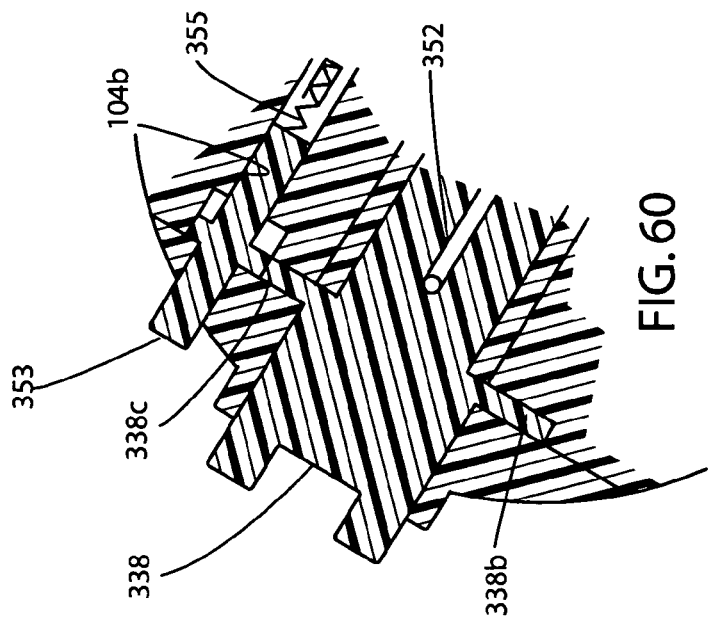
FIG. 60 is a cross-sectional view taken along lines 60-60 of FIG. 58.

As illustrated in FIGS. 58 and 60 of the drawings, dose control indexing means are provided to lock the patient dose selector knob 338 in any selected position. In the present form of the invention this dose control indexing means comprises a locking plunger 353 that is received within a bore 104b formed in the forward portion 104 of housing 102. Locking plunger 353 is continuously biased outwardly by a coiled spring 355 into locking engagement with a selected one of a plurality of circumferentially spaced apart cutouts 338c formed in the flange portion 338b of the patient dose selector knob assembly 338. With this construction, in order to rotate the patient dose selector knob 338 from a selected position, the locking plunger 353 must be manually pushed inwardly against the urging of spring 355.

Figure 61:
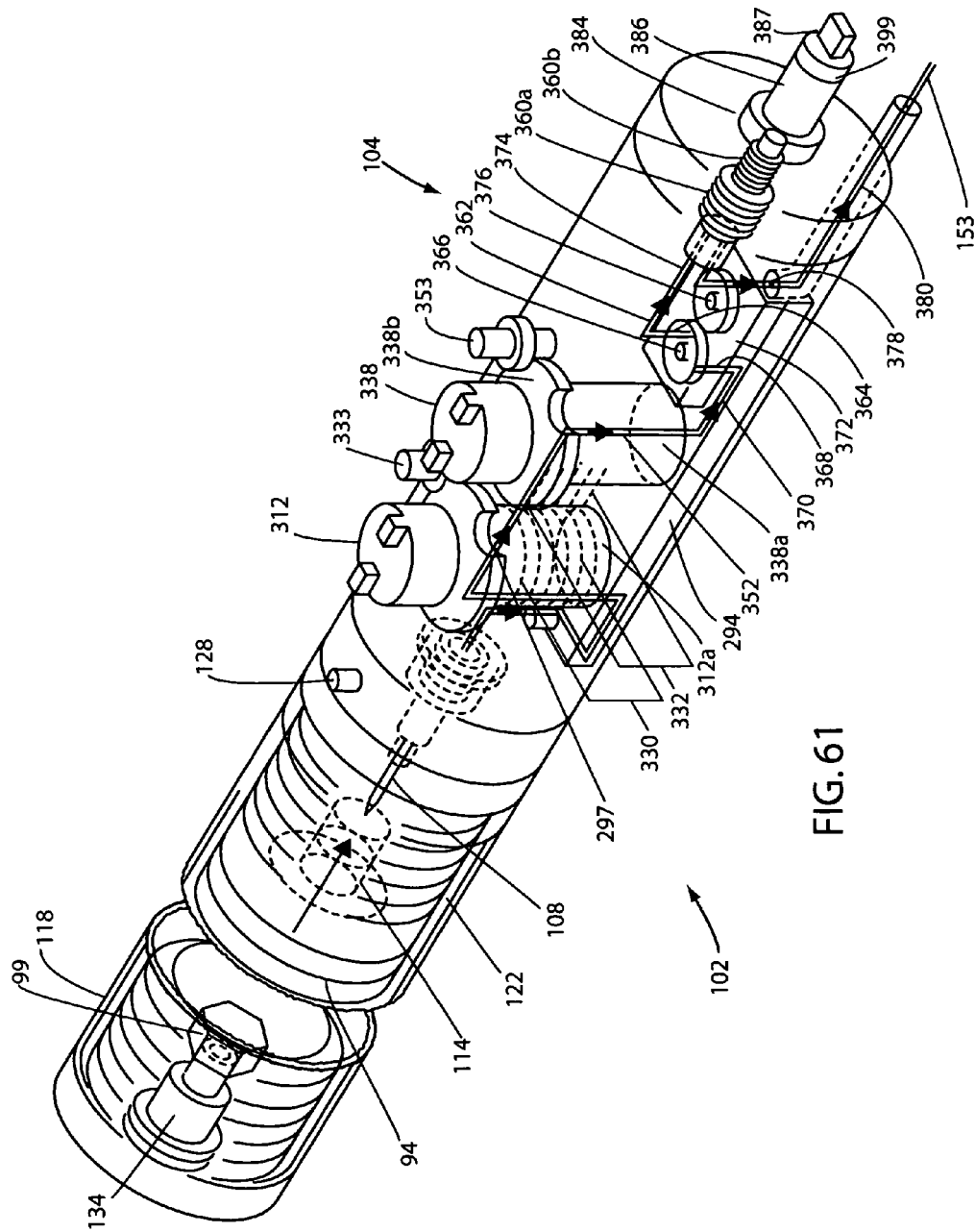
FIG. 61 is a generally perspective, diagrammatic view illustrating the path of fluid flow through the device during the fluid delivery step.
Figure 64:
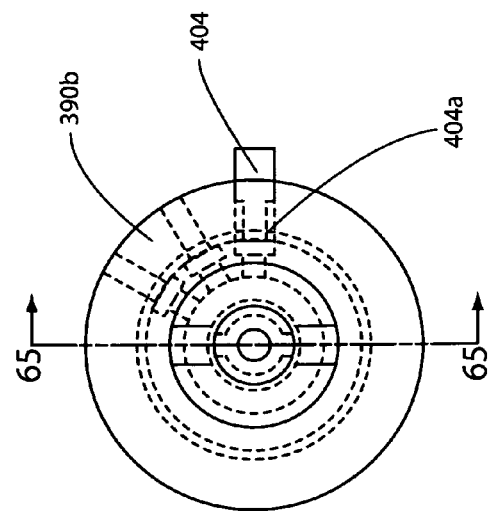
FIG. 64 is an end view of the fluid delivery device shown in FIG. 1.
Figure 68:
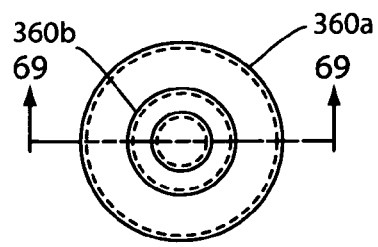
FIG. 68 is a top plan view of the bolus reservoir of the apparatus.
Figure 69:
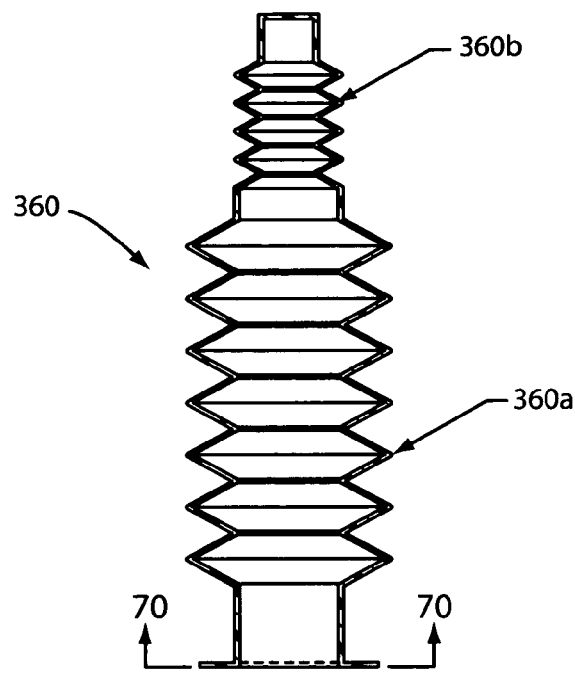
FIG. 69 is a cross-sectional view taken along lines 69-69 of FIG. 68.
Figure 70:
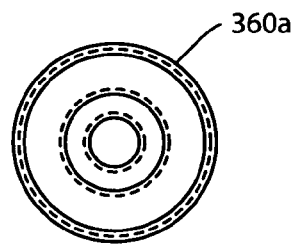
FIG. 70 is a view taken along lines 70-70 of FIG. 69.
Figure 71:
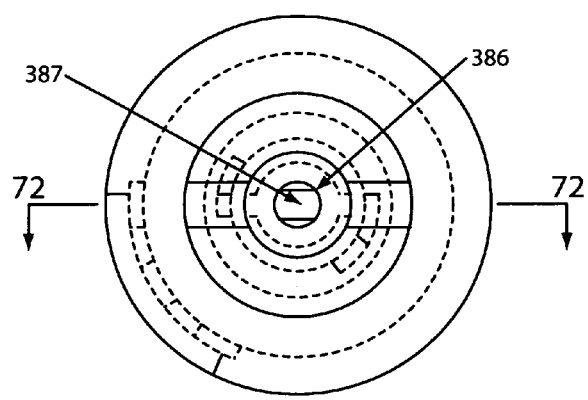
FIG. 71 is a top plan view of the bolus selector subassembly of the apparatus.

Considering further the bolus delivery means of the invention, this novel means, which is housed within forward portion 104 of housing 102, includes a double bolus reservoir 360 (FIGS. 68, 69 and 70) that is disposed within a cavity 359 formed in forward portion 104 of housing 102. The double bolus reservoir 360 is defined by interconnected, collapsible bellows structures 360a and 360b that are in communication with passageway 352 of the dose control means via a longitudinally extending passageway 362, a vertical stub passageway 364, a conventional umbrella check valve 366, a vertical stub passageway 368 and a longitudinal passageway 370 (see FIGS. 21 and 61). Umbrella check valve 366, which is carried with an internal housing 372, functions to permit fluid flow toward reservoir 360, but blocks fluid flow in the opposite direction. Reservoir 360 is in fluid communication with the administration set 153 (FIG. 1) via passageway 374, a second conventional umbrella check valve 376, a vertical passageway 378 and longitudinally extending passageway 380. With this construction, low flow from the dose control means any selected dose, to bolus reservoir 360 and then on to the patient via the administration set 153 which here comprises a conventional "Y" site injection septum or port 153a, a conventional gas vent and particulate filter 153b, a line clamp 153c and a conventional luer connector 153d.

Figure 66:
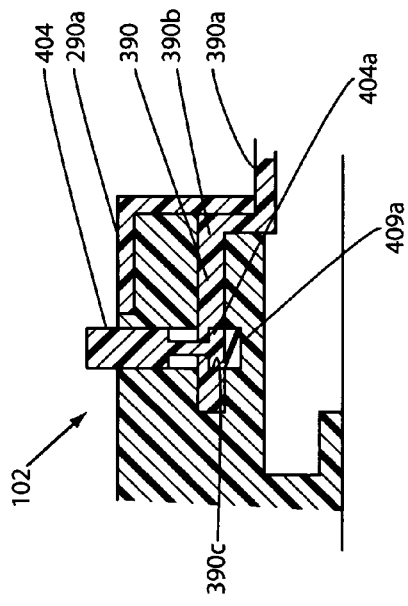
FIG. 66 is a fragmentary cross-sectional view illustrating the construction of the bolus interlock mechanism of the fluid delivery device.
Figure 65:
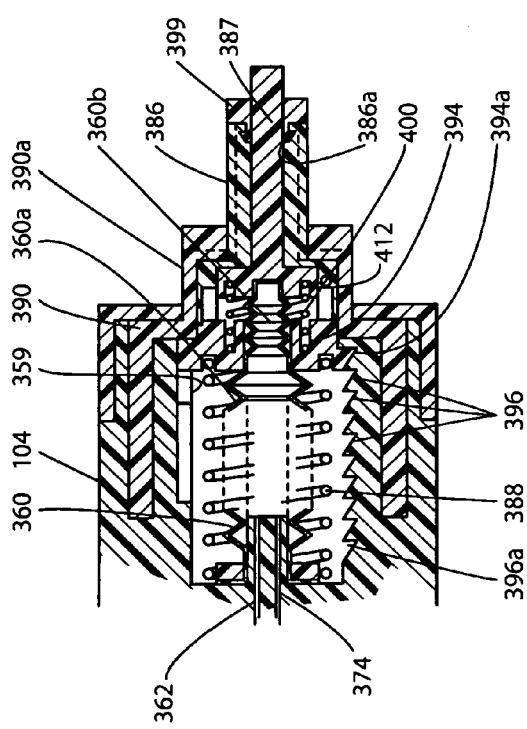
FIG. 65 is a cross-sectional view taken along lines 65-65 of FIG. 64 illustrating the construction of the bolus operating mechanism of the fluid delivery device.
Figure 67:
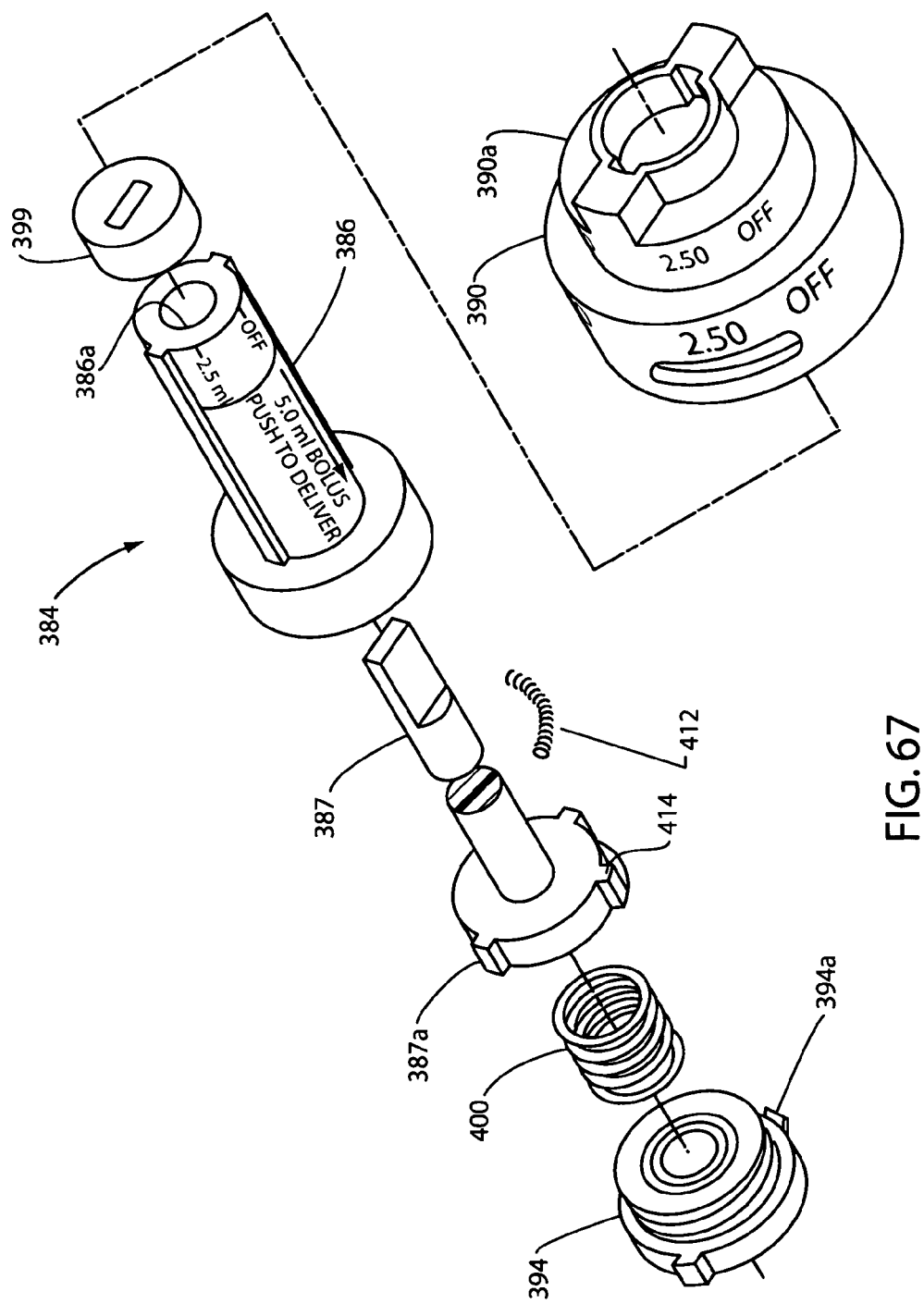
FIG. 67 is a generally perspective, exploded view of the bolus operating mechanism.
Figure 72:
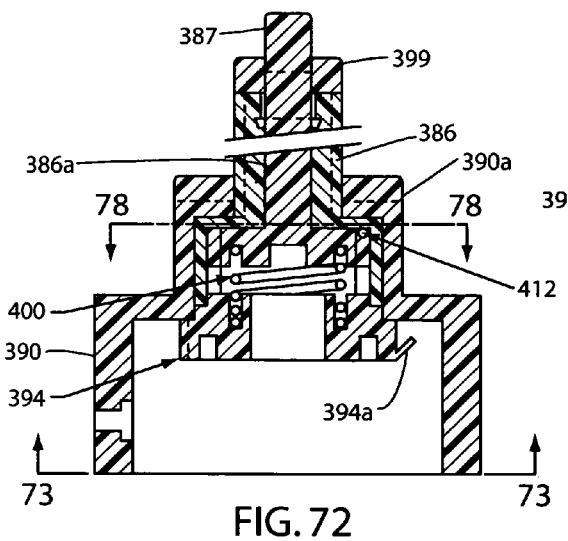
FIG. 72 is a cross-sectional view taken along lines 72-72 of FIG. 71 illustrating the construction of the main bolus and secondary plunger assembly portion of the bolus operating mechanism.
Figure 73:
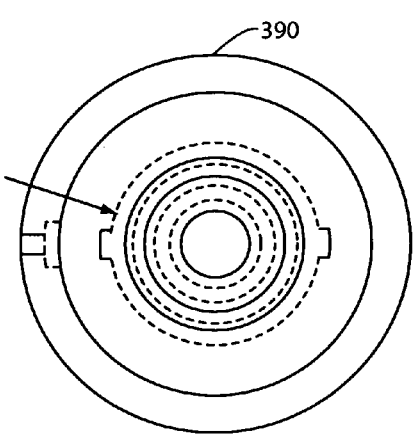
FIG. 73 is a view taken along lines 73-73 of FIG. 72.
Figure 74:
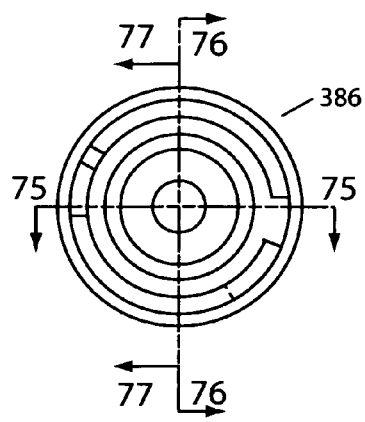
FIG. 74 is a top view of the main reservoir operating shaft.
Figure 75:
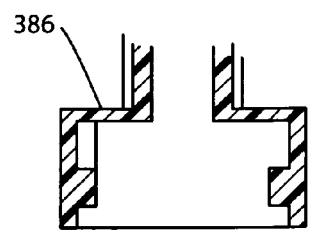
FIG. 75 is a cross-sectional view taken along lines 75-75 of FIG. 74.
Figure 76:
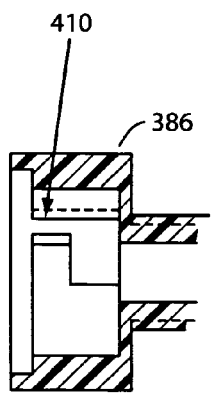
FIG. 76 is a cross-sectional view taken along lines 76-76 of FIG. 74.
Figure 77:
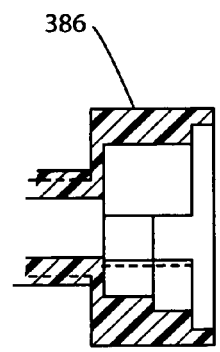
FIG. 77 is a cross-sectional view taken along lines 77-77 of FIG. 74.

Referring particularly to FIGS. 61, and 63 through 67, the important bolus operating mechanism of the invention is there shown and generally designated by the numeral 384. This mechanism permits selected bolus doses of medicaments to be delivered to the patient from reservoir 360 as may be required. As best seen in FIGS. 65 and 67 of the drawings, this novel mechanism here comprises a first, or main operating shaft 386 for controllably collapsing the bellows structure 360a and a second operating shaft 387 (FIGS. 71, 72, 83 and 84) for controllably collapsing the bellows structure 360b (see FIG. 69). By way of non limiting example, bellows structure 360a can have a first volume of between approximately 3 ml and approximately 6.0 ml while bellows structure 360b can have a second, lesser volume of approximately 0.5 ml and approximately 2.0 ml. Main operating shaft 386 controllably collapses bellows structure 360a by pushing inwardly on the shaft against the urging of a coiled operating spring 388 that circumscribes bellows structure 360a. In the manner illustrated in FIG. 65, main operating shaft 386 is movable within the reduced diameter portion 390a of the bolus selector housing 390 that is carried within the forward portion 104 of housing 102. Following rotation of the bolus selector in a manner presently to be described, the main operating shaft can be moved inwardly against the urging of coiled operating spring 388 from an extended to an inward position. Inward movement of the main operating shaft causes inward movement of a pusher member 394 which, in turn, causes the collapse of the bellows portion 360a. It is to be noted that pusher member 394 is provided with a yieldably deformable locking tab 394a (see also FIG. 72) that is adapted to engage a plurality of generally saw-toothed shaped protuberances 396 that are formed on the inner wall of cavity 359. Locking tab 394a is so constructed and arranged as to ride over protuberances 396 as the main operating shaft is pushed inwardly of cavity 359. However, the saw-toothed protuberances 396 are configured so that the locking tab will engage the vertical faces 396a of the protuberances in a manner to prevent movement of the pusher member in a direction toward its starting position. With this construction, once the reservoir bellows portion 360a is collapsed, it will remain in a collapsed configuration.

Following rotation of the operating knob 399 of the bolus operating mechanism 384 in a manner presently to be described, second operating shaft 387 can be moved inwardly within a bore 386a provided in main operating shaft 386 against the urging of a second coil spring 400. Second operating shaft 387 operates against bellows portion 360b in a manner to collapse the bellows portion as the second operating shaft is urged inwardly against the urging of spring 400. As the bellows portion 360b collapses, medicinal fluid contained there within will be urged outwardly of the reservoir via outlet passageway 378. However, upon the release of inward pressure exerted against second operating shaft 387, spring 400 will urge the operating shaft into its original starting position so that subsequent smaller bolus doses of medicament can be delivered to the patient.

Turning now to FIGS. 87, 88 and 89, in delivering bolus doses of medicament to the patient, a locking member 404 that is carried by housing 102 in the manner shown in FIG. 66 of the drawings must be pushed inwardly in order to permit rotation of the reduced diameter portion 390a of the bolus selector housing 390. As indicated in FIG. 66, inward movement of the locking member causes the locking shoulder 404a to move out of locking engagement with a cavity 390c formed in the enlarged diameter portion 390b of the bolus selector housing 390 so as to permit rotation of the bolus selector housing 390. With the locking member pushed inwardly, the bolus selector housing 390 can be rotated from the "off" position shown in FIG. 87 of drawings to the "5.0 ml" position. This done, the main operating shaft can be pushed inwardly causing plunger 394 to collapse bellows 360a, resulting in the delivery of a bolus dose of a predetermined volume of medicament to the patient (in this case 5.0 ml). As previously mentioned, once the main operating shaft is pushed inwardly, it will be locked in position by locking tab 394a.

When it is desired to deliver a smaller bolus dose of medicament to the patient, as, for example 2.5 ml, it is necessary to first rotate cap 399 from the "off" position shown in FIG. 87 to the "2.5 ml" position shown in FIG. 88. As best seen in FIG. 83 second operating shaft 387 is provided with a rotational stop 387a that engages a stop wall 410 provided on the main operating shaft 390 (see FIGS. 74 through 77). As the second operating shaft is rotated, a coiled spring 412 carried a spring shelf 414 (FIGS. 83, 84 and 86) will resist the rotation and will be compressed in the manner in FIG. 80.

This done, the secondary operating shaft 387 can be pushed inwardly in the manner illustrated in FIG. 89. This inward movement of the second operating shaft will collapse bellows portion 360b causing the fluid contained there within (in this instance 2.5 ml) to be delivered to the patient via outlet passageway 374.

With the construction described in the preceding paragraph, when the rotational forces exerted on cap 399 cease, spring 412 will urge the cap to return to its starting position and at the same time, spring 400 will urge shaft 387 into its starting position, thereby permitting a repeated application of a smaller bolus dose of medicament to the patient as may be required.

Having now described the invention in detail in accordance with the requirements of the patent statutes, those skilled in this art will have no difficulty in making changes and modifications in the individual parts or their relative assembly in order to meet specific requirements or conditions. Such changes and modifications may be made without departing from the scope and spirit of the invention, as set forth in the following claims.

The invention claimed is:

1. A dispensing device for dispensing medicaments to a patient comprising:
   (a) a device housing;
   (b) a carriage assembly disposed within said device housing for movement between a first position and a second position;
   (c) an aseptically filled collapsible container carried by said carriage assembly, said collapsible container being formed by a blow-fill-seal process and having a continuous wall including a collapsible side wall, a pierceable top wall connected to said collapsible side wall;
   (d) a stored energy means operably associated with said carriage assembly for moving said carriage assembly between said first and second positions, said stored energy means comprising a coil spring having a first end in engagement with said device housing and a second end in engagement with said carriage;
   (e) an administration set, including an administration line interconnected with said collapsible container;
   (f) fluid flow control means carried by said device housing for controlling the flow of medicament from said collapsible container toward said administration line, said flow control means comprising dose control means for controlling the dose of medicament delivered to the patient and rate control means for controlling the rate of medicament flow from said collapsible reservoir toward said dose control means; and
   (g) a bolus delivery assembly carried by said device housing and in communication with said administration set for delivering bolus doses of medication to said administration set, said bolus delivery assembly comprising:
      (i) a collapsible bolus container having a first portion of a first volume and a second portion of a second lesser volume;
      (ii) a first mechanism for collapsing said first portion of said collapsible container; and
      (iii) a second mechanism for collapsing said second portion of said collapsible container.

2. The dispensing device as defined in claim 1 in which said dose control means includes dose selector means for selecting the medicament dose delivered to said administration line, said dose selector means comprising a selector housing carried by said device housing and a selector member rotatably carried by said selector housing.

3. The dispensing device as defined in claim 1, further including locking means carried by said device housing for locking said carriage assembly in said first position.

4. The dispensing device as defined in claim 1 in which said rate control means includes selector means for selecting the rate of fluid flow between said collapsible container and said administration set.

5. The dispensing device as defined in claim 1 in which said rate control means comprises a rate control plate having a plurality of fluid flow channels interconnected with said collapsible container; and operating means carried by said device housing for controlling fluid flow between said collapsible container and said rate control means.

6. The dispensing device as defined in claim 5 in which said operating means comprises a piercing member for piercing said top wall of said collapsible container.

7. A dispensing device for dispensing medicaments to a patient comprising:
   (a) a device housing;
   (b) a carriage assembly disposed within said device housing for movement between a first position and a second position;
   (c) an aseptically filled collapsible container carried by said carriage assembly, said collapsible container being formed by a blow-fill-seal process and having a continuous wall including a collapsible side wall, a pierceable top wall connected to said collapsible side wall;
   (d) a stored energy means operably associated with said carriage assembly for moving said carriage assembly between said first and second positions, said stored energy means comprising a coil spring having a first end in engagement with said device housing and a second end in engagement with said carriage;
   (e) an administration set, including an administration line interconnected with said collapsible container;
   (f) fluid flow control means carried by said device housing for controlling the flow of medicament from said collapsible container toward said administration line, said flow control means comprising dose control means for controlling the dose of medicament delivered to the patient and rate control means for controlling the rate of medicament flow from said collapsible reservoir toward said dose control means, said rate control means comprising selector means for selecting the rate of fluid flow between said collapsible container and said administration set and a rate control plate having a plurality of fluid flow channels interconnected with said collapsible container; and
   (g) a bolus delivery assembly carried by said device housing and in communication with said administration set for delivering bolus doses of medicament to said administration set, said bolus delivery assembly comprising a collapsible bolus container having a first portion of a first volume and second portion of a second lesser volume, said bolus delivery assembly further including a first mechanism for collapsing said first portion of said collapsible bolus container and a second mechanism for collapsing said second portion of said collapsible bolus container.

8. The dispensing device as defined in claim 7 in which said first portion of said collapsible bolus container has a volume of between about 3 ml and about 6 ml in which said second portion of said collapsible bolus container has a volume of between about 0.5 ml and about 3 ml.

9. The dispensing device as defined in claim 7 further including operating means carried by said device housing for controlling fluid flow between said collapsible container and said rate control means, said operating means comprising a piercing member for piercing said top wall of said collapsible container.

* * * * *